US009035095B2

(12) United States Patent
Mori et al.

(10) Patent No.: US 9,035,095 B2
(45) Date of Patent: May 19, 2015

(54) PROCESSES FOR PRODUCING SUCCINIC ACID

(75) Inventors: Yoshiaki Mori, Yokkaichi (JP); Go Takahashi, Yokkaichi (JP); Hideki Suda, Tokyo (JP); Shuji Yoshida, Tokyo (JP)

(73) Assignee: MITSUBISHI CHEMICAL CORPORATION, Tokyo (JP)

( * ) Notice: Subject to any disclaimer, the term of this patent is extended or adjusted under 35 U.S.C. 154(b) by 85 days.

(21) Appl. No.: 13/617,503

(22) Filed: Sep. 14, 2012

(65) Prior Publication Data

US 2013/0018206 A1 Jan. 17, 2013

Related U.S. Application Data

(63) Continuation of application No. PCT/JP2011/056103, filed on Mar. 15, 2011.

(30) Foreign Application Priority Data

| Mar. 16, 2010 | (JP) | 2010-059578 |
| Mar. 17, 2010 | (JP) | 2010-060674 |
| Apr. 1, 2010 | (JP) | 2010-085561 |
| Apr. 7, 2010 | (JP) | 2010-089048 |
| Aug. 11, 2010 | (JP) | 2010-179896 |

(51) Int. Cl.
*C07C 51/42* (2006.01)
*C07C 51/43* (2006.01)
*C12P 7/46* (2006.01)

(52) U.S. Cl.
CPC .. *C07C 51/43* (2013.01); *C12P 7/46* (2013.01)

(58) Field of Classification Search
CPC .................................................. C07C 51/42
USPC ......................................................... 562/593
See application file for complete search history.

(56) References Cited

U.S. PATENT DOCUMENTS

| 4,950,806 | A | 8/1990 | Iimuro et al. |
| 5,168,055 | A | 12/1992 | Datta et al. |
| 5,948,949 | A | 9/1999 | Takagawa et al. |
| 5,958,744 | A | 9/1999 | Berglund et al. |
| 6,265,190 | B1 | 7/2001 | Yedur et al. |
| 6,284,904 | B1 | 9/2001 | Ponnampalam |
| 6,334,878 | B1 | 1/2002 | Miyahara et al. |
| 6,451,109 | B1 | 9/2002 | Ueno et al. |
| 2001/0049456 | A1 | 12/2001 | Fushihara et al. |
| 2006/0276674 | A1 | 12/2006 | Kushiku et al. |
| 2007/0015836 | A1 | 1/2007 | Rose |
| 2008/0194876 | A1 | 8/2008 | Cervenka et al. |

FOREIGN PATENT DOCUMENTS

| JP | 44-29246 | 11/1969 |
| JP | 56-011797 | 2/1981 |
| JP | 1-316335 | 12/1989 |
| JP | 3-30685 | 2/1991 |
| JP | 9-249586 | 9/1997 |
| JP | 11-292816 | 10/1999 |
| JP | 2001-514900 | 9/2001 |
| JP | 2001-322964 | 11/2001 |
| JP | 2002-505310 | 2/2002 |
| JP | 2003-012623 | 1/2003 |
| JP | 2004-358351 A | 12/2004 |
| JP | 2005-082498 | * 3/2005 |
| JP | 2005-333886 | 12/2005 |
| JP | 2006-528966 | 12/2006 |
| JP | 2007-261957 | 10/2007 |
| JP | 2008-049304 | 3/2008 |
| JP | 2008-297251 | 12/2008 |
| JP | 2009-011873 | 1/2009 |
| JP | 2009-502911 | 1/2009 |
| WO | 98/37938 A1 | 9/1998 |
| WO | 01/14307 | 3/2001 |
| WO | 2005/030973 | 4/2005 |

OTHER PUBLICATIONS

International Search Report issued Apr. 26, 2011 in PCT/JP2011/056103 filed Mar. 15, 2011.
Crystal Growth & Design (U.S.A.), 2002, 2, pp. 449-452.
Information Offer Form dated Nov. 26, 2014 issued in corresponding Japanese patent application No. 2012-505708 (with English translation).
Office Action dated Feb. 17, 2015 issued in corresponding Japanese patent application No. 2012-505708 (with English translation).

* cited by examiner

*Primary Examiner* — Yong Chu
*Assistant Examiner* — Sonya Wright
(74) *Attorney, Agent, or Firm* — Oblon, McClelland, Maier & Neustadt, L.L.P.

(57) ABSTRACT

Provided are processes for producing high-purity succinic acid from a succinic-acid-containing liquid through crystallization.

15 Claims, 15 Drawing Sheets

10: CRYSTALLIZER
1: TANK
4: ROTATING BLADE
3: ROTATING BLADE
2: DRAFT TUBE

SEQUENCE LISTING

```
<160> NUMBER OF SEQ ID NOS: 9

<210> SEQ ID NO 1
<211> LENGTH: 24
<212> TYPE: DNA
<213> ORGANISM: Artificial sequence
<220> FEATURE:
<223> OTHER INFORMATION: primer

<400> SEQUENCE: 1
acgaagtgac tgctatcacc cttg                                          24

<210> SEQ ID NO 2
<211> LENGTH: 23
<212> TYPE: DNA
<213> ORGANISM: Artificial sequence
<220> FEATURE:
<223> OTHER INFORMATION: primer

<400> SEQUENCE: 2
cagaacttta ctgcatccgc aca                                           23
```

<210> SEQ ID NO 3
<211> LENGTH: 36
<212> TYPE: DNA
<213> ORGANISM: Artificial sequence
<220> FEATURE:
<223> OTHER INFORMATION: primer

<400> SEQUENCE: 3
gtggatgaga caggactatc tagagctaca gtgaca                              36

<210> SEQ ID NO 4
<211> LENGTH: 33
<212> TYPE: DNA
<213> ORGANISM: Artificial sequence
<220> FEATURE:
<223> OTHER INFORMATION: primer

<400> SEQUENCE: 4
agaattgatt ataggtcact aaaactaatt cag                                 33

<210> SEQ ID NO 5
<211> LENGTH: 25
<212> TYPE: DNA
<213> ORGANISM: Artificial sequence
<220> FEATURE:
<223> OTHER INFORMATION: primer

<400> SEQUENCE: 5
gtaggtatca cccatgcaca agttg                                          25

<210> SEQ ID NO 6
<211> LENGTH: 23
<212> TYPE: DNA
<213> ORGANISM: Artificial sequence
<220> FEATURE:
<223> OTHER INFORMATION: primer

<400> SEQUENCE: 6
cctagtatcg taaccccga ttc                                             23

<210> SEQ ID NO 7
<211> LENGTH: 21
<212> TYPE: DNA
<213> ORGANISM: Artificial sequence
<220> FEATURE:
<223> OTHER INFORMATION: primer

<400> SEQUENCE: 7
gttttcccag tcacgacgtt g                                              21

<210> SEQ ID NO 8
<211> LENGTH: 24
<212> TYPE: DNA
<213> ORGANISM: Artificial sequence
<220> FEATURE:
<223> OTHER INFORMATION: primer

<400> SEQUENCE: 8
actggcattg atgtcgatcc agca                                           24

<210> SEQ ID NO 9
<211> LENGTH: 23
<212> TYPE: DNA
<213> ORGANISM: Artificial sequence
<220> FEATURE:

```
<223> OTHER INFORMATION: primer

<400> SEQUENCE: 9
ctgttgccaa tttgcgaagc tca                                              23
```

PROCESSES FOR PRODUCING SUCCINIC ACID

TECHNICAL FIELD

The present invention relates to processes for industrially producing succinic acid, which is useful as a food additive, a starting material for medicines, a starting material for resins, etc.

BACKGROUND ART

Succinic acid is industrially used extensively as a food additive, starting material for medicines, starting material for resins, etc. Hitherto, succinic acid has been obtained by reducing petroleum-derived maleic anhydride or maleic acid. Recently, however, it has been reported that succinic acid is produced, in a high carbon yield, from a wide range of biomass-derived starting materials by a fermentation operation using microorganisms. Especially when succinic acid is to be used as a starting material for polymers, high-purity succinic acid is required for the purposes of maintaining the degrees of polymerization of the polymers, preventing the polymers from taking a color, etc.

Known as a process for producing succinic acid is, for example, a process in which maleic anhydride or maleic acid each derived from a petrochemical starting material is reduced into succinic acid in an aqueous solution and the resultant aqueous solution is cooled to cause crystallization and thereby obtain the succinic acid as crystal particles (for example, patent document 1). However, patent document 1 includes no statement concerning any method for crystallizing succinic acid.

Known as processes for producing succinic acid by fermentation are, for example, a process in which the calcium salt of succinic acid is decomposed with sulfuric acid (for example, patent document 2), a process in which an ion-exchange resin is used (for example, patent documents 3 and 4), a process in which ammonium hydrogen sulfate and/or sulfuric acid is added to the ammonium salt of succinic acid to yield succinic acid and ammonium sulfate (for example, patent document 5), and a process in which electrodialysis is used (for example, patent document 6). However, none of patent documents 2 to 6 includes a statement concerning a detailed crystallization method for recovering crystals of succinic acid.

With respect to crystallization operations, known techniques include a method in which the particle diameter and particle size distribution of succinic acid are regulated by regulating the stirring conditions and the degree of supersaturation (for example, patent document 7) and a method in which the particle diameter and particle size distribution of succinic acid are regulated by using seed crystals (for example, non-patent document 1). However, these methods each relate to the regulation of particle diameter and particle size distribution, and there is no statement therein concerning the purity of succinic acid.

Meanwhile, it is important, for the recovery of succinic acid through crystallization, to regulate the particle diameter and particle size distribution of the crystals, and various attempts have been made (for example, patent documents 8 and 9).

For example, patent document 8 describes a technique for obtaining purified succinic acid from a succinic-acid-containing fermentation broth produced by a fermentation method, the technique including adding an inorganic acid to the fermentation broth, from which cells of the microorganism have been removed beforehand, to adjust the pH of the fermentation broth to 4.0 or less and thereby temporarily precipitate the succinic acid, subsequently heating the liquid to partly dissolve and melt the succinic acid, thereafter cooling the mixture with stirring to precipitate crystals, and separating the crystals [from page (2), left upper column, line 14 to the same page, right upper column, line 3]. It is important that the fermentation broth which has undergone the acid precipitation treatment should be subjected to a heat treatment as described above. In case where the heat treatment is omitted, the crystallization results in flaky and fine crystals. In contrast, when the heat treatment is conducted, granular and large crystals are obtained by the crystallization [page (3), left upper column, lines 6-9].

Patent document 9 includes a statement to the effect that in a method for crystallizing succinic acid from a succinic-acid-containing solution, crystals having a large particle diameter and a narrow particle diameter distribution can be obtained by regulating the required-stirring-power ratio (Pv) to 70-350 $W/m^3$ and the nondimensional degree of supersaturation (Sc) to 1-1.3 (claim 1 and paragraph 0009).

In patent document 8 and patent document 9, crystallization of succinic acid is conducted by a batch treatment.

PRIOR-ART DOCUMENTS

Patent Documents

Patent Document 1: JP-B-44-292466
Patent Document 2: JP-A-3-030685
Patent Document 3: JP-T-2002-505310 (The term "JP-T" as used herein means a published Japanese translation of a PCT patent application.)
Patent Document 4: International Publication No. 05/030973
Patent Document 5: JP-T-2001-514900
Patent Document 6: JP-A-2005-333886
Patent Document 7: JP-A-2005-82498
Patent Document 8: JP-A-56-11797
Patent Document 9: JP-A-2005-082498

Non-Patent Document

Non-Patent Document 1: Crystal Growth & Design (U.S.A.), (2002), 2, pp.449-452

SUMMARY OF THE INVENTION

Problems that the Invention is to Solve

A subject for the invention is to provide a process for efficiently and stably producing high-purity succinic acid from a succinic-acid-containing liquid or a succinic-acid-containing liquid through crystallization. There is a need for a method for regulating the particle diameter and particle size distribution of crystals in a crystallization treatment of succinic acid, and an object of the invention is to provide a process for producing succinic acid which has a narrow particle size distribution and excellent handleability.

Means for Solving the Problems

The present inventions diligently made investigations in order to accomplish the subject. As a result, the inventors have found that the subject can be accomplished with the processes described below. Namely, essential points of the invention reside in the following.

1. A process for producing succinic acid which comprises crystallizing succinic acid from a succinic-acid-containing liquid with stirring in a crystallization tank equipped with a stirrer, wherein a power required for the stirring per unit volume of the succinic-acid-containing liquid in the crystallization tank is 0.4-3 kW/m$^3$.
2. A process for producing succinic acid which comprises crystallizing succinic acid from a succinic-acid-containing liquid in a crystallization tank,
    wherein the process comprises a crystallization step in which the succinic acid that has crystallized is discharged continuously or intermittently from the crystallization tank and a succinic-acid-containing liquid is fed continuously or intermittently to the crystallization tank, to keep the liquid level of the crystallization tank so as to be within a given range.
3. A process for producing succinic acid which comprises a crystallization step of producing solid succinic acid from a succinic-acid-containing liquid in a crystallization tank equipped with a stirrer, wherein the process comprises: discharging the crystallized succinic acid continuously or intermittently from the crystallization tank; feeding a succinic-acid-containing liquid continuously or intermittently to the crystallization tank to keep the liquid level of the crystallization tank so as to be within a given range; and conducting an operation, during at least one part of the crystallization step, under a stirring condition of a power required for stirring per unit volume of the succinic-acid-containing liquid of 0.4-3 kW/m$^3$.
4. The process for producing succinic acid according to the item 2 or 3 above, wherein an operation is conducted so that the succinic-acid-containing liquid in the crystallization tank has a temperature of 25-60° C.
5. The process for producing succinic acid according to the item 4 above, wherein during the crystallization, a difference between a temperature of the succinic-acid-containing liquid present in the crystallization tank and a temperature at which the succinic-acid-containing liquid introduced into the crystallization tank becomes a saturated succinic acid solution, is 10-45° C.
6. The process for producing succinic acid according to any one of the items 2 to 5 above, wherein the succinic-acid-containing liquid has an average residence time in the crystallization tank of 1-5 hours.
7. The process for producing succinic acid according to any one of the items 2 to 6 above, which comprises a pressure reduction step of reducing an internal pressure of the crystallization tank, during the crystallization operation, to a value lower than the pressure of the ambient atmosphere.
8. The process for producing succinic acid according to the item 7 above, wherein the internal pressure of the crystallization tank is 0.5-20 kPa.
9. The process for producing succinic acid according to any one of the items 2 to 8 above, wherein in the crystallization step, seed crystals of succinic acid are introduced continuously or intermittently into the crystallization tank.
10. The process for producing succinic acid according to the item 9 above, wherein the seed crystals comprise crystals obtained by pulverizing at least one part of the succinic acid which has been discharged from the crystallization tank.
11. The process for producing succinic acid according to the item 10 above, wherein the pulverization is conducted with a wet pulverizer.
12. The process for producing succinic acid according to the item 10 or 11 above, wherein the pulverization is conducted with at least one selected from between a circulation unit for discharging a succinic-acid slurry present in the crystallization tank and returning the slurry to the inside of the crystallization tank and a pump disposed in a unit for feeding a succinic-acid-containing liquid to the crystallization tank.
13. The process for producing succinic acid according to any one of the items 9 to 12 above, wherein the seed crystals have a volume-average particle diameter of 200 μm or less, and an amount of the seed crystals is 0.001-20% by weight of the amount of the succinic acid recovered.
14. The process for producing succinic acid according to any one of the items 1 to 13 above, wherein the succinic-acid-containing liquid has a succinic-acid concentration of 10-45% by weight.
15. The process for producing succinic acid according to any one of the items 1 to 14 above, wherein the succinic-acid-containing liquid includes a solvent, the solvent being a liquid having a relative permittivity of 10 or higher.
16. The process for producing succinic acid according to any one of the items 1 to 15 above, wherein when the crystallization is conducted, the succinic-acid-containing liquid is cooled by at least 10° C. from the temperature which the succinic-acid-containing liquid had when introduced into the crystallization tank.
17. The process for producing succinic acid according to any one of the items 1 to 16 above, wherein the succinic-acid-containing liquid is fed to a liquid phase present in the crystallization tank.
18. The process for producing succinic acid according to any one of the items 1 to 17 above, wherein the liquid present in the crystallization tank has a temperature which is lower than the temperature of the wall surface of the crystallization tank.
19. Succinic acid produced by the process for producing succinic acid according to any one of the items 1 to 18 above, wherein when approximating a particle diameter distribution by the Rosin-Rammier distribution, a uniformity number n is 3.0 or greater.
20. The succinic acid according to the item 19 above, which has a weight-basis median diameter of 400 μm or less.

Effects of the Invention

According to the processes of the invention, high-purity succinic acid can be produced from a succinic-acid-containing liquid through crystallization. According to the processes of the invention, succinic acid which is highly uniform in particle diameter and has excellent powder handleability and which has a high purity can be stably produced highly efficiently. Furthermore, according to the processes of the invention, succinic acid which has a particle size distribution that is narrow and imparts excellent handleability to the succinic acid can be obtained by crystallizing succinic acid continuously and stably.

MODES FOR CARRYING OUT THE INVENTION

Figure 1:
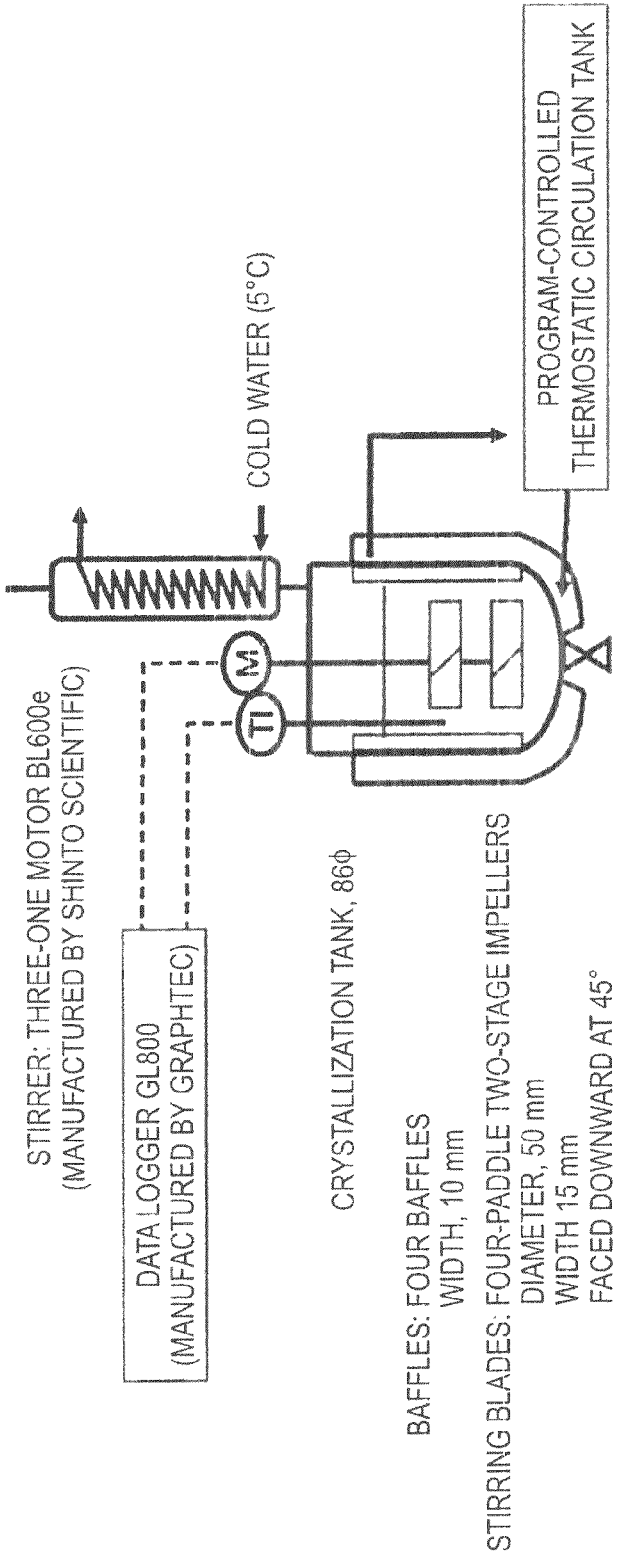
FIG. 1 is a drawing which shows the crystallizer used in Examples 1-1 to 1-3.

Embodiments of the invention will be explained below in detail. However, the following explanations on constituent elements are for representative embodiments of the invention, and the embodiments can be variously modified unless the modifications depart from the spirit of the invention. In the invention, the expression "% by weight" has the same meaning as "% by mass".

One of the processes for producing succinic acid of the invention is a process for producing succinic acid which comprises crystallizing succinic acid from a succinic-acid-containing liquid with stirring in a crystallization tank equipped with a stirrer, and which is characterized in that the stirring of the succinic-acid-containing liquid in the crystallization tank is conducted at a power required for stirring per unit volume of the succinic-acid-containing liquid of 0.4-3 kW/m$^3$.

Another process for producing succinic acid of the invention is a process for producing succinic acid which comprises crystallizing succinic acid from a succinic-acid-containing liquid in a crystallization tank, and which is characterized by including a crystallization step in which the succinic acid that has crystallized is discharged continuously or intermittently from the crystallization tank and a succinic-acid-containing liquid is fed continuously or intermittently to the crystallization tank to keep the liquid level of the crystallization tank so as to be within a given range.

<Succinic-Acid-Containing Liquid>

In the production processes of the invention, the term "succinic-acid-containing liquid" has the same meaning as "succinic-acid-containing fluid" and "succinic-acid-containing solution". The succinic-acid-containing liquid to be subjected to crystallization may have any configuration so long as the liquid contains succinic acid.

The succinic-acid-containing liquid may be a solution which contains succinic acid dissolved therein or may be a solution in which succinic acid in a salt form has been dissolved. Alternatively, the succinic-acid-containing liquid may be a slurry in which solid succinic acid or a solid salt of succinic acid coexists with either of those solutions, or may be a slurry in which a solid substance which is not succinic acid coexists with either of those solutions.

Any solvent can be used in the succinic-acid-containing liquid so long as succinic acid or the salt of succinic acid is soluble therein and as the solvent is liquid under the conditions to be used for the crystallization operation.

From the standpoint of efficiently recovering the succinic acid and/or succinic acid salt during the crystallization, solvents which have a large temperature dependence of solubility are preferred. Preferred of these are solvents having a relative permittivity of 10 or higher. More preferred are solvents having a relative permittivity of 20 or higher. Especially preferred are solvents having a relative permittivity of 50 or higher.

More specific examples thereof include ketone solvents such as acetone, nitrogen-containing solvents such as acetonitrile and N,N-dimethylformamide, carboxylic acid solvents such as formic acid, alcohol solvents such as ethanol, methanol, and 1-propanol, and water.

Examples of the solution which contains succinic acid dissolved therein include: an aqueous succinic acid solution obtained by hydrotreating maleic anhydride or maleic acid in an aqueous solution thereof in the presence of a metal catalyst, e.g., palladium; and an aqueous solution of either succinic acid or a succinic acid salt each obtained from a biomass-derived starting material.

The succinic-acid-containing liquid is not particularly limited, and may be a succinic-acid-containing liquid obtained by hydrogenerating a petrochemical starting material, e.g., maleic anhydride, or may be a succinic-acid-containing liquid which is derived from a biomass-derived starting material. In recent years, succinic acid can be produced from a wide range of biomass-derived starting materials by a fermentation operation in a high carbon yield using microorganisms. Consequently, when environmental burden, etc. are taken into account, a succinic-acid-containing liquid obtained from a biomass-derived starting material is preferred.

The term "succinic-acid-containing liquid obtained from a biomass-derived starting material" means a liquid which contains succinic acid induced from a biomass-derived starting material. Examples of the biomass-derived starting material include wood, rice straw, rice hulls, rice bran, long-stored rice, corn, sugar canes, cassava, sago palms, bean curd refuse, corncobs, tapioca refuse, bagasse, vegetable oil refuse, potatoes, buckwheat, soybeans, oils and fats, old newspapers, papermaking residues, aquatic-product residues, livestock excreta, sewage sludge, and waste foods.

Preferred of these are plant resources such as wood, rice straw, rice hulls, rice bran, long-stored rice, corn, sugar canes, cassava, sago palms, bean curd refuse, corncobs, tapioca refuse, bagasse, vegetable oil refuse, potatoes, buckwheat, soybeans, oils and fats, old newspapers, and papermaking residues. More preferred are wood, rice straw, rice hulls, long-stored rice, corn, sugar canes, cassava, sago palms, potatoes, oils and fats, old newspapers, and papermaking residues. Most preferred are corn, sugar canes, cassava, and sago palms.

These biomass-derived starting materials generally contain nitrogen element or many alkali metals and alkaline earth metals including Na, K, Mg, and Ca.

These biomass-derived starting materials are induced to carbon sources through known steps for pretreatment/saccharification, such as, for example, a chemical treatment with an acid, alkali, etc., a biological treatment with a microorganism, and a physical treatment, without particular limitations.

Those steps are not particularly limited, and examples thereof include a size reduction step in which a biomass-derived starting material is reduced into a small size by chipping, shaving, mashing, etc. Examples thereof optionally further include a pulverization step in which the starting material is treated with a grinder or a mill. The biomass-derived starting material which has been thus reduced in size is further subjected to steps for pretreatment/saccharification and thereby inducted to a carbon source.

Specific examples of methods for the pretreatment/saccharification steps include: chemical methods such as an acid treatment with a strong acid, e.g., sulfuric acid, nitric acid, hydrochloric acid, or phosphoric acid, an alkali treatment, ammonia freezing/steam explosion, solvent extraction, treatment with a supercritical fluid, and treatment with an oxidizing agent; physical methods such as pulverization, steam explosion, microwave treatment, and irradiation with electron beams; and biological treatments such as hydrolysis by a treatment with a microorganism or enzyme.

Examples of the carbon sources induced from those biomass-derived starting materials include di- and polysaccharides such as hexoses, e.g., glucose, mannose, galactose, fructose, sorbose, and tagatose, pentoses, e.g., arabinose, xylose, ribose, xylulose, and ribulose, maltose, sucrose, lactose, trehalose, starch, and cellulose, fatty acids such as butyric acid, caproic acid, caprylic acid, capric acid, lauric acid, myristic acid, palmitic acid, palmitoleic acid, stearic acid, oleic acid, linoleic acid, linolenic acid, monocutin acid, arachidic acid, eicosanic acid, arachidonic acid, behenic acid, erucic acid, docosapentaenoic acid, docosahexaenoic acid, lignoceric acid, and selacholeic acid, and fermentable sugars of polyalcohols such as glycerol, mannitol, xylitol, and ribitol. Preferred of these are glucose, maltose, fructose, sucrose, lactose, trehalose, and cellulose.

Succinic acid is synthesized from those carbon sources by a fermentation method based on a microbial conversion, a chemical conversion method including a reaction step such as hydrolysis, dehydration reaction, hydration reaction, oxidation reaction, or reduction reaction, or a combination of the fermentation method and the chemical conversion method. Preferred of these is a fermentation method based on a microbial conversion by a microorganism having the ability to produce succinic acid.

The microorganism having the ability to produce succinic acid is not particularly limited so long as the microorganism has the ability to produce succinic acid. Examples thereof include enteric bacteria such as *Escherichia coli*, bacteria belonging to the genus *Bacillus*, and Coryneform bacteria. It is preferred to use an aerobic microorganism, a facultative anaerobic microorganism, or a microaerophilic microorganism among those microorganisms.

Examples of the aerobic microorganism include Coryneform bacteria, bacteria belonging to the genus *Bacillus*, bacteria belonging to the genus *Rhizobium*, bacteria belonging to the genus *Arthrobacter*, bacteria belonging to the genus *Mycobacterium*, bacteria belonging to the genus *Rhodococcus*, bacteria belonging to the genus *Nocardia*, and bacteria belonging to the genus *Streptomyces*. More preferred of these are Coryneform bacteria.

The Coryneform bacteria are not particularly limited so long as the bacteria are classified as the group. Examples thereof include bacteria belonging to the genus *Corynebacterium*, bacteria belonging to the genus *Brevibacterium*, and bacteria belonging to the genus *Arthrobacter*.

Preferred of these are bacteria belonging to the genus *Corynebacterium* or *Brevibacterium*. More preferred are bacteria classified as *Corynebacterium glutamicum*, *Brevibacterium flavum*, *Brevibacterium ammoniagenes*, and *Brevibacterium lactofermentum*.

Furthermore, it is preferred to employ a strain which has enhanced pyruvate carboxylase activity and reduced lactate dehydrogenase activity, as in the Examples which will be given later.

Reaction conditions for the microbial conversion, such as reaction temperature and pressure, depend on the activity of the microorganism to be selected, such as cells, mold, etc. Conditions suitable for obtaining succinic acid may be selected according to each case.

In microbial conversions, as the pH decreases, the microorganisms decrease in metabolic activity or become dormant, resulting in an impaired product yield or in the death of the microorganisms. Consequently, a neutralizer is usually used.

Usually, the pH of the system is measured with a pH sensor, and the pH is regulated so as to be within a given pH range by adding a neutralizer. The pH value is regulated so as to be within a range where the activity of the microorganism used, e.g., cells or mold, is most effectively exhibited, according to the kind of the microorganism. Methods for adding a neutralizer are not particularly limited, and either continuous addition or intermittent addition may be used.

Examples of the neutralizer include ammonia, ammonium carbonate, urea, the hydroxides of alkali metals, the hydroxides of alkaline earth metals, the carbonates of alkali metals, and the carbonates of alkaline earth metals. Preferred of these are ammonia, ammonium carbonate, and urea.

Examples of the hydroxides of alkali (alkaline earth) metals include NaOH, KOH, $Ca(OH)_2$, $Mg(OH)_2$, and the like and mixtures thereof. Examples of the carbonates of alkali (alkaline earth) metals include $Na_2CO_3$, $K_2CO_3$, $CaCO_3$, $MgCO_3$, $NaKCO_3$, and the like and mixtures thereof.

It is preferred that the fermentation broth obtained through a microbial conversion should be used after the microorganism has been removed therefrom. Although methods for removing the microorganism are not particularly limited, use may be made, for example, of separation by sedimentation, centrifugal separation, separation by filtration, or a method including a combination of these. Industrially, the microorganism is removed by a method such as centrifugal separation or separation by membrane filtration.

In the centrifugal separation, use can be made of centrifugal sedimentation, centrifugal filtration, or the like. The operating conditions to be used for the centrifugal separation are not particularly limited. However, it is usually preferred to conduct the separation at a centrifugal force of 100-100,000 G. The operation can be continuous or batchwise.

In the separation by membrane filtration, use can be made, for example, of microfiltration and/or ultrafiltration. The material of the membrane is not particularly limited, and examples thereof include organic membranes such as polyolefins, polysulfones, polyacrylonitrile, and poly(vinylidene fluoride) and membranes made of inorganic materials such as ceramics.

As an operation mode, either the dead-end type or the cross-flow type can be used. In the separation by membrane filtration, there frequently are cases where the membrane is clogged with the microorganism. Use may hence be made, for example, of a method in which the microorganism is roughly removed by centrifugal separation or another technique before membrane filtration is conducted.

Furthermore, the fermentation broth from which the microorganism has been removed may be suitably concentrated from the standpoint of the operation and efficiency of the purification step to be conducted later. Although methods for the concentration are not particularly limited, examples thereof include a method in which an inert gas is passed, a method in which the water is distilled off by heating, a method in which the water is distilled off at a reduced pressure, and a method in which these techniques are conducted in combination. The concentration operation may be a batch operation or a continuous operation.

(Protonation)

In the case where a neutralizer was used in the fermentation step as described above, a salt of succinic acid is obtained. When the salt of succinic acid obtained is present in the aqueous solution, this salt is stably present in the water. It is therefore preferred to convert the salt to succinic acid.

Namely, an acid is added to the succinic acid salt to conduct salt interchange and thereby convert the salt to succinic acid. This conversion hereinafter is often referred to as protonation, and this step hereinafter is often referred to as protonation step.

The acid to be used in the protonation step usually is an acid which is stronger than succinic acid, because this acid is required to undergo salt interchange with the succinic acid salt. Namely, an acid which has a lower acid dissociation constant pKa than succinic acid is used, and an acid having a pKa less than 4 is usually used. Furthermore, an inorganic acid is preferred to an organic acid, as the acid to be used.

Addition of an inorganic acid to the succinic acid salt results in the formation of an inorganic salt as a by-product. For example, when ammonia was used as a neutralizer in the fermentation operation, the succinic acid is present as an ammonium salt. In this case, when sulfuric acid is used in this step, ammonium sulfate generates as a by-product salt.

The amount of the acid to be used depends on the acidity of the acid. However, it is usually preferred to add an acid in an amount of about 0.1-5 equivalents to the amount of the cation as a component of the succinic acid salt.

It is usually preferred to regulate the addition of an acid in terms of pH. It is preferred to adjust the pH to a value which is equal to or lower than the acidity pKa of succinic acid, although the pH value depends on the pKa. Usually, it is preferred to conduct the operation at a pH of 4 or less.

Meanwhile, even when an acid is added in excess, the decrease in pH gradually becomes smaller and the excess acid does not undergo salt interchange with the succinic acid salt but remains in the acid form in the system. The excess acid necessitates a neutralization treatment or the like, making the step inefficient. It is therefore preferred to usually regulate the pH to 1 or higher.

(Concentration Treatment)

Since the succinic-acid-containing liquid obtained from a biomass-derived starting material generally has a low succinic-acid concentration, a concentration operation usually is necessary. The degree of concentration is not particularly limited. However, it is preferred that the final concentrate should have a succinic-acid solubility which is not higher than the saturation solubility and is as close as possible to the saturation solubility.

The succinic-acid concentration of the succinic-acid-containing liquid to be fed to the crystallization tank is preferably 10-45% by weight, more preferably 15-40% by weight, even more preferably 20-35% by weight.

By regulating the succinic-acid concentration of the succinic-acid-containing liquid to 10% by weight or higher, a high succinic-acid yield is attained in the crystallization operation and the operation is rendered efficient. When the succinic-acid concentration thereof has been regulated to 45% by weight or less, dissolution of the succinic acid and handling of the resultant solution do not require a high temperature, and the handling is easy.

The temperature of the succinic-acid-containing liquid is not particularly limited so long as the conditions are capable of resulting in a temperature difference which makes it possible to recover the succinic acid in the crystallization step. From the standpoints of the recovery of succinic acid, purity of the succinic acid to be obtained, etc., the difference between the temperature of the liquid which is being introduced into the crystallization tank and the temperature of the liquid during crystallization is usually preferably 10-90° C., more preferably 20-80° C., even more preferably 30-70° C., although that difference depends on the concentration of succinic acid.

By regulating the temperature difference to 10° C. or more, an increase in the recovery of succinic acid is attained to render the operation efficient. When the temperature difference is 90° C. or less, the resultant slurry does not have too high a concentration and is easy to handle. As a result, the particles of succinic acid obtained can have improved uniformity and an improved succinic-acid purity.

<Crystallization Tank>

The crystallization tank to be used in the invention is not particularly limited in the structure thereof so long as the tank is a vessel equipped with a stirrer. Although a vessel which has a usually known stirrer can be used, a cylindrical vessel having a bottom is preferred. It is preferred to dispose baffles in the tank in order to efficiently shear the succinic-acid-containing liquid. Furthermore, it is also possible to use a vessel which has a cylindrical guide, e.g., a guide called draft tube, in order to regulate the flow within the crystallization tank.

The shape of the vessel is not particularly limited. However, from the standpoints of rendering the slurry more even in the device and efficiently shearing the slurry, the ratio between the diameter and height of the vessel (L/D) is usually preferably 0.5-3, more preferably 0.7-2.5, even more preferably 1-2.

<Stirrer>

The stirrer to be used in the invention is a stirrer which is equipped with one or more stirring blades.

The stirring blades need not be special blades, and known stirring blades can be used. Examples thereof include shearing blades such as paddle blades and turbine blades, sweep-back blades, and discharge blades such as Pfaudler impellers, Maxblend Blade (registered trademark of Sumitomo Heavy Industries, Ltd.), and Fullzone Blade (registered trademark of Shinko-Pantec Co., Ltd.). In the invention, however, it is preferred to use shearing blades such as paddle blades and turbine blades in order to efficiently transfer the power.

With respect to distinction between shearing blades and discharge blades, blades can be evaluated, for example, in terms of the ratio of power number Np to discharge quantity number Nqd, i.e., Np/Nqd (see, for example, *Bessatu Kagaku Kōgyō* 23-2, *Sekkei/Sōsa Shirīzu No. 1, Kaitei Kakuhan Sōchi*, pp.21-25 and 38-39). Here, it is preferred that blades should be selected from blades which satisfy Np/Nqd≥1.7, preferably from blades which satisfy Np/Nqd≥2.

The size of the stirring blades also is not particularly limited. In the invention, another stirrer, such as a stirrer for circulating the succinic-acid-containing liquid, may be used besides the stirrer equipped with stirring blades. As the other stirrer, use can be made, for example, of a device by which the succinic-acid-containing liquid that has been led out of the crystallization tank is circulated to the crystallization tank by means of a pump for fluid transfer, e.g., a centrifugal pump.

<Stirring>

In the invention, the succinic-acid-containing liquid in the crystallization tank is subjected to crystallization under such stirring conditions that the power required for stirring per unit volume of the succinic-acid-containing liquid (hereinafter often referred to as Pv) is 0.4-3 kW/m$^3$.

By regulating the Pv to 0.4 kW/m$^3$ or higher, the crystals of succinic acid can be made of have an improved purity. The reason why the use of a Pv regulated to 0.4 kW/m$^3$ or higher brings about an improvement in the purity of the succinic acid crystals is thought to be that the contents of the tank are sufficiently stirred and, hence, the crystals are prevented from aggregating while taking some of the mother liquor therein.

On the other hand, by regulating the Pv to 3 kW/m$^3$ or less, energy is prevented from being wasted on the crystallization and the crystals of succinic acid are prevented from being obtained as too small crystals and adversely affecting the subsequent solid-liquid separation step. Furthermore, in the case where the crystallization is conducted at ordinary pressure, it is possible to prevent the trouble that the gas introduced into the liquid from the gas phase by the stirring adheres to succinic acid and this succinic acid rises to the liquid surface to constitute an obstacle to the crystallization operation.

<Crystallization>

The crystallization in the invention is an operation in which the solubility of the succinic acid is changed by causing the succinic-acid-containing liquid to undergo some change and crystals of succinic acid are thereby precipitated from the succinic-acid-containing liquid. This crystallization may be conducted by any method so long as the operation is capable of precipitating the succinic acid as crystals from the succinic-acid-containing liquid.

More specifically, examples of crystallization methods include: a cooling crystallization method in which the internal pressure of the crystallization tank is reduced to thereby change the temperature of the succinic-acid-containing liquid and precipitate the succinic acid while utilizing the temperature dependence of the solubility of the succinic acid in the solvent; a concentration crystallization method in which the solvent is volatilized from the solution, for example, by heating and a pressure reduction to heighten the succinic-acid concentration of the succinic-acid-containing liquid and thereby precipitate the succinic acid; a poor-solvent crystallization method in which a third ingredient (poor solvent) which lowers the solubility of the succinic acid is added to the succinic-acid-containing liquid to precipitate the succinic acid; and a method which includes a combination of these.

In the case where the succinic-acid-containing liquid contains a salt of succinic acid, a strong acid such as sulfuric acid or hydrochloric acid may be added to the succinic-acid-containing liquid. Thus, the succinic acid salt can be converted to succinic acid in the non-dissociated form, and crystals of the succinic acid can be precipitated using this technique in combination with any of methods including the cooling, concentration, and poor-solvent addition described above.

With respect to the cooling crystallization, examples of cooling methods for use therein include a method in which the succinic-acid-containing liquid is cooled by circulating the liquid through an external heat exchanger or the like, a method in which a tube for passing a coolant therethrough (inner coil) is introduced into the succinic-acid-containing liquid, and a method in which the internal pressure of the apparatus is reduced to thereby volatilize the solvent contained in the solution and cool the liquid by means of the heat of vaporization of the solvent.

Preferred of these is the method in which the internal pressure of the apparatus is reduced to thereby volatilize the solvent contained in the solution and cool the liquid by means of the heat of vaporization of the solvent. This is because succinic acid can be prevented from precipitating at the heat-exchange interface and thereby inhibiting thermal transfer. In addition, that method is preferred also from the standpoint of crystallization yield because the cooling is accompanied with concentration of the succinic acid contained in the solution.

The temperature of the succinic-acid-containing liquid present in the crystallization tank during the crystallization (hereinafter, that temperature is often referred to as crystallization temperature) is set at a temperature which enables crystals of succinic acid to separate out of the succinic-acid-containing liquid.

The crystallization temperature is usually preferably 25-60° C., more preferably 30-50° C., from the standpoints that the recovery of succinic acid can be heightened and that when the succinic acid is used as a starting material for a polymer, the polymer can be inhibited from taking a color. Furthermore, it is preferred that the difference between the crystallization temperature and the temperature at which the succinic-acid-containing solution introduced into the crystallization tank becomes a saturated succinic acid solution should be 10-45° C.

By regulating the crystallization temperature to 25° C. or higher, the polymer obtained using the recovered succinic acid as a starting material therefor can be inhibited from taking a color.

By regulating the crystallization temperature to 60° C. or lower, use of the recovered succinic acid as a starting material for a polymer is prevented from posing the problem that the polymer takes a color. In addition, the recovery of succinic acid in the crystallization step is improved and succinic acid can be produced efficiently.

Meanwhile, in the method in which the succinic-acid-containing liquid is cooled by passing a coolant through a jacket or an inner coil, the difference in temperature between the succinic-acid slurry present on the heat transfer surface and the coolant is prevented from becoming too large and considerable scaling can be prevented.

There is a clear correlation between the crystallization temperature and the degree of coloration of the polymer obtained using the recovered succinic acid as a starting material therefor. It is thought that some impurity remains in the succinic acid as a result of a decrease in crystallization temperature and serves as a cause of coloration during the polymerization. However, the causative substance is unknown at present.

In the method in which the succinic-acid-containing liquid is cooled by passing a coolant through a jacket or an inner coil, the difference in temperature between the succinic-acid slurry present on the heat transfer surface and the coolant is usually preferably 20° C. or less, more preferably 10° C. or less, from the standpoint of preventing scaling.

It is preferred that the temperature of the wall surface of the crystallization tank should be kept higher than the crystallization temperature. By regulating the temperature of the wall surface of the crystallization tank so as to be higher than the crystallization temperature, succinic acid is prevented from depositing on the crystallization wall surface, making it possible to stably and continuously operate the apparatus. It is therefore possible to prevent the trouble that the succinic acid which has deposited on the wall surface periodically peels off and falls into the crystallization tank and thereby renders the purity of succinic acid unstable or reduced.

It is preferred that the internal pressure of the crystallization tank during the crystallization should be kept lower than the pressure of the ambient atmosphere. By regulating the internal pressure of the crystallization tank so as to be lower than the pressure of the ambient atmosphere, the solvent in the solution can be volatilized to heighten the succinic-acid concentration and the succinic-acid-containing liquid can be cooled by means of the heat of vaporization of the solvent. The succinic acid can be thus crystallized.

Furthermore, by regulating the internal pressure of the crystallization tank so as to be lower than the pressure of the ambient atmosphere, the inhibition of heat transfer due to the deposition of succinic acid on the heat-exchange interface can be prevented as compared, for example, with the method in which the succinic-acid-containing liquid is cooled by heat exchange. In addition, it is possible to prevent the succinic acid which has deposited on the heat-exchange interface from taking therein an impurity contained in the succinic-acid-containing liquid and to control the rate at which solid succinic acid is precipitated. It is also possible to control aggregation of the precipitated solid. Thus, it is possible to obtain solid succinic acid which is prevented from including any impurity which was contained in the succinic-acid-containing liquid, and production of succinic acid having a higher purity is rendered possible.

For regulating the internal pressure of the crystallization tank so as to be lower than the pressure of the ambient atmosphere, any method may be used so long as the internal pressure of the crystallization tank can be regulated so as to be lower than the pressure of the ambient atmosphere when crystals of succinic acid are precipitated from the succinic-acid-containing liquid. For example, a vacuum device can be utilized.

The internal pressure of the crystallization tank in the method in which crystallization is conducted at a reduced pressure is determined by the desired crystallization temperature. The internal pressure thereof is usually preferably 0.5-20 kPa, more preferably 1-20 kPa, even more preferably 1-15 kPa, especially preferably 1.5-10 kPa.

In the case where the solvent is, for example, water, the internal pressure of the crystallization tank is usually preferably 3-20 kPa, more preferably 4-15 kPa, especially preferably 5-10 kPa.

By regulating the pressure thereof to 0.5 kPa or higher, the slurry in the crystallization tank is prevented from coming to have too high a concentration depending on the concentration of the succinic-acid-containing liquid which is fed, making it easy to handle the slurry. In addition, pressure control is easy. Furthermore, there are no limitations on equipment for pressure reduction, and a reduction in equipment cost can generally be attained. Use of that internal pressure hence is preferred from the standpoint of profitability. For example, in case where steam ejectors are employed for pressure reduction, an increase in the degree of vacuum results in an increased equipment cost, for example, because of the necessity of an increase in the number of stages of steam ejectors.

On the other hand, by regulating the pressure so as to be lower than the pressure of the ambient atmosphere, the internal temperature of the crystallization tank is inhibited from rising. In addition, the slurry in the crystallization tank is prevented from having too low a concentration, resulting in an improvement in efficiency.

The vacuum device can be selected from known techniques while taking account of the desired pressure, whether or not there is a solvent which vaporizes together with the water, the kind of the solvent, etc. The known techniques include the techniques enumerated, for example, in *Sekkei/Sōsa Shirīzu No. 3, Kaitei Shōseki* (Kagaku Kogaku Sha) pp.292-293. Examples thereof include water or steam ejectors, oil-sealed rotary vacuum pumps, and the like.

In the crystallization operation, it is preferred to regulate the nucleation and crystal growth of the succinic acid in order to regulate the particle size distribution of the crystals of succinic acid. The nucleation and crystal growth of the succinic acid are regulated usually by regulating the degree of supersaturation with succinic acid within the tank. For attaining this regulation, use is usually made of a method in which crystallization period is regulated. The crystallization period is regulated usually preferably to 0.5-10 hours, more preferably to 1-5 hours.

By regulating the crystallization period so as to be not shorter than the lower limit, the degree of supersaturation with succinic acid within the tank is prevented from becoming too high and fine crystals are inhibited from generating. In addition, it is possible to prevent, for example, the trouble that the slurry in the state of still having a degree of supersaturation is discharged from the crystallization tank and thereby causes scaling in succeeding steps. When the crystallization period is regulated so as to be not longer than the upper limit, use of an unnecessarily large crystallization tank is avoided and the operation is efficient.

For example, in the case of batch cooling crystallization, it is preferred that the succinic-acid-containing liquid should be cooled to a given temperature over 0.5-5 hours and then aged for 0.1-5 hours. In this operation, the rate of cooling the succinic-acid-containing liquid is usually preferably 0.05-2° C./min, more preferably 0.1-1.5° C./min, even more preferably 0.2-1° C./min.

The crystallization can be conducted continuously by continuously or intermittently feeding the succinic-acid-containing liquid so as not to make the crystallization tank empty, crystallizing the succinic acid in the crystallization tank, and continuously or intermittently discharging from the crystallization tank the succinic-acid slurry which includes both the yielded succinic acid and a succinic-acid-containing liquid.

The succinic-acid-containing liquid may be fed to the crystallization tank in any desired amount at any desired time so long as the crystallization tank does not become empty. However, the feed rate is regulated so that the amount of the contents does not exceed the effective capacity of the crystallization tank. Unlike batch operations, which have limitations with respect to scale, such a continuous operation is an operation that is necessary and indispensable to large- and industrial-scale crystallization operations required to attain high production efficiency.

There are no particular limitations on methods for feeding the succinic-acid-containing liquid. Examples of the methods include a method in which the succinic-acid-containing liquid is sent with a liquid feed pump and a method in which the succinic-acid-containing liquid is sent by means of pressure.

With respect to the rate of feeding the succinic-acid-containing liquid, it is preferred to feed the succinic-acid-containing liquid so that the succinic-acid-containing liquid has an average residence time in the crystallization tank of 1-5 hours.

By regulating the average residence time thereof so as to be not less than the lower limit, the degree of supersaturation with succinic acid within the tank is prevented from becoming too high and fine crystals are inhibited from generating. In addition, it is possible to prevent, for example, the trouble that the slurry in the state of still having a degree of supersaturation is discharged from the crystallization tank to thereby cause scaling in succeeding steps. When the average residence time thereof is regulated so as to be not longer than the upper limit, use of an unnecessarily large crystallization tank is avoided and the operation is efficient.

It is preferred that the succinic-acid-containing liquid should be fed to the liquid-phase part within the crystallization tank, the liquid-phase part being constituted of a slurry. By feeding the succinic-acid-containing liquid to the liquid-phase part within the crystallization tank, fine crystals of succinic acid can be prevented from generating in a large amount and troubles such as, for example, pipe clogging can be prevented from arising.

(Discharge of Succinic-Acid Slurry)

When the succinic acid obtained is to be discharged from the crystallization tank during the crystallization conducted in the continuous mode, the succinic acid may be discharged as a slurry together with a succinic-acid-containing liquid. The discharge may be conducted in any desired amount at any desired time unless the crystallization tank becomes empty. This discharge is performed, for example, by a method in which the slurry is discharged continuously or intermittently, for example, with a slurry pump or by means of pressure sending, in which the slurry is sent, by means of a pressure difference, to a receiver tank having a lower pressure than the crystallization tank, while suitably comparing the discharge amount with the amount of the fed succinic-acid-containing liquid so that the crystallization tank does not become empty.

Examples of methods for feeding the succinic-acid-containing liquid to the crystallization tank and discharging a slurry from the crystallization tank so that the crystallization tank does not become empty include: a method in which the rate of feeding and the rate of discharge are regulated so as to be the same; and a method in which an operation is repeated in which the succinic-acid-containing liquid is fed when the liquid level within the crystallization tank has declined to or below a given level and a slurry is discharged when the liquid level has risen to or above a given level, with the aid of a liquid-level sensor or the like.

<Solid-Liquid Separation>

The succinic acid discharged from the crystallization tank is usually taken out as a mixture thereof with a succinic-acid-containing liquid. Consequently, the succinic acid usually is separated from the succinic-acid-containing liquid in a solid-liquid separation step. In the solid-liquid separation step, the mixture is subjected to solid-liquid separation by a conventionally known method to separate the mixture into the crystals of succinic acid and the mother liquor.

The method for solid-liquid separation is not particularly limited so log as the method is capable of separating the succinic acid from the succinic-acid-containing liquid. Examples thereof include separation by filtration, separating by sedimentation, and centrifugal separation. The operation may be batchwise or continuous. Examples of efficient solid-liquid separators include continuous centrifugal separators and centrifugal settlers such as decanters.

It is also preferred, from the standpoint of heightening the purity of the succinic acid to be obtained, that the solid matter separated by the solid-liquid separation operation should be rinsed with, for example, cold water to remove the succinic-acid-containing liquid adherent to the surface thereof.

<Drying>

Since a succinic-acid-containing liquid is usually adherent to the surface of the succinic acid obtained in the solid-liquid separation step, the succinic acid is rinsed with, for example, cold water according to need and is then dried. Thus, succinic acid is obtained. Methods for the drying are not particularly limited, and examples include convective heat transfer type dryers such as band dryers and fluidized-bed dryers and conductive heat transfer type dryers such as drum dryers.

Especially preferred is a fluidized-bed dryer which is capable of large-quantity continuous treatment and which is less apt to cause crystal breakage or the like during the drying. When a fluidized-bed dryer is used, it is preferred to dry the succinic acid while supplying nitrogen thereto and to regulate the atmosphere so as to have an oxygen concentration of 12% or less, from the standpoint of preventing the succinic acid from causing dust explosion.

With respect to the temperature of the succinic acid during the drying, the succinic acid is dried so that the temperature thereof is preferably 100° C. or lower, more preferably 90° C. or lower, even more preferably 80° C. or lower, because there is a possibility that succinic anhydride might generate as a result of intramolecular dehydration.

The succinic acid obtained by the production processes of the invention has a weight-basis particle diameter distribution which, when approximated by the Rosin-Rammler distribution, has a uniformity number n of preferably 3.0 or greater, more preferably 3.0-6.0, especially preferably 3.2-5.0. The average particle diameter thereof is preferably 400 μm or less, more preferably 100-300 μm. The term "average particle diameter" herein means a weight-basis median diameter obtained through sieve classification.

<Example of Process for Producing Succinic Acid by Vaporization Crystallization>

Figure 13:
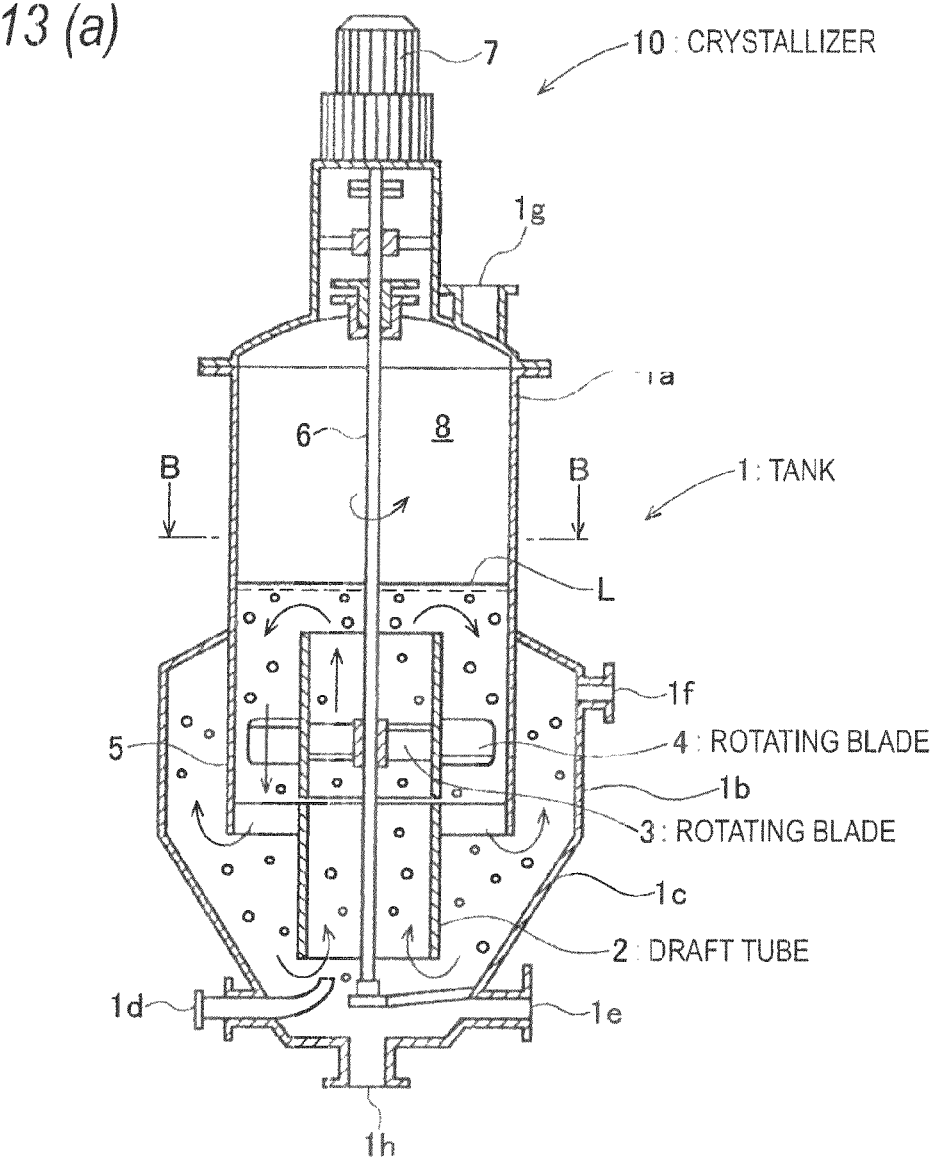
FIGS. 13 (*a*) and (*b*) are diagrammatic sectional views of a crystallizer for use in a process for producing succinic acid according to an embodiment.
Figure 13:
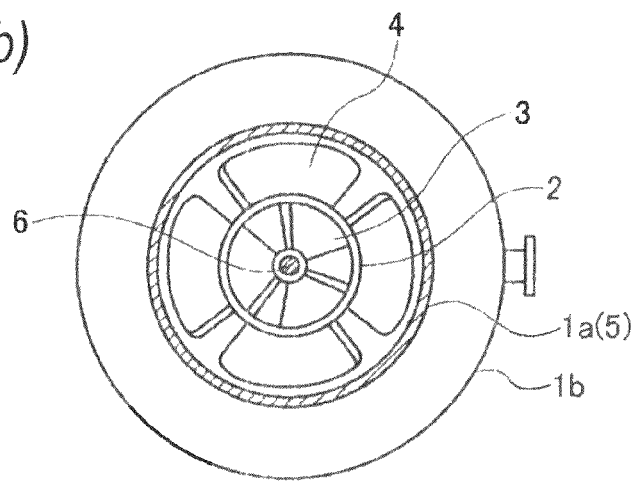
Figure 14:
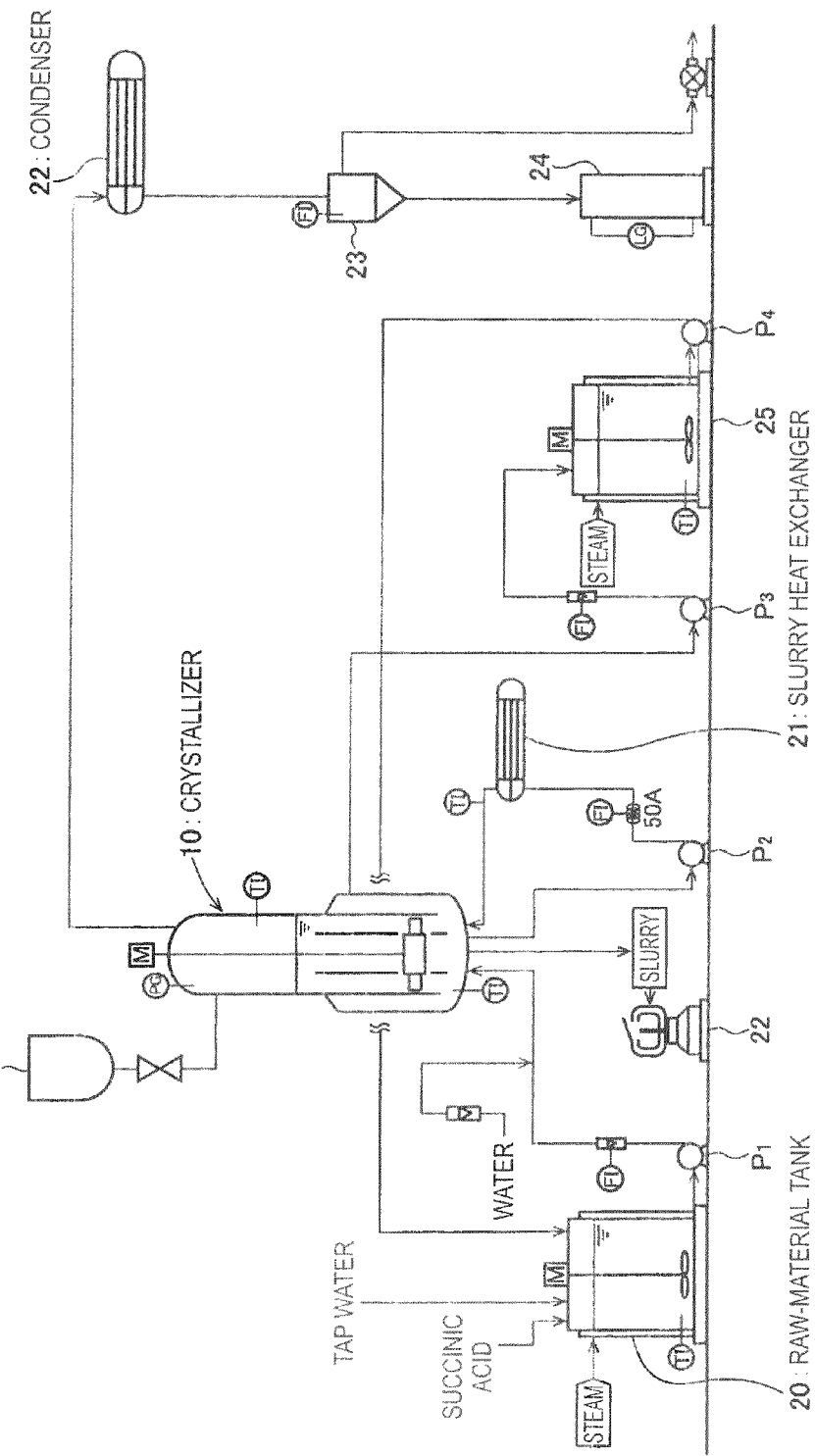
FIG. 14 is a flow diagram for illustrating the process for producing succinic acid according to an embodiment.

An example of processes for producing succinic acid by vaporization crystallization is explained below by reference to FIG. 13 and FIG. 14. FIG. 13(a) is a diagrammatic sectional view of a crystallizer for use in a process for succinic-acid production according to an embodiment, and FIG. 13(b) is a horizontal sectional view taken on the line B-B of FIG. 13(a). FIG. 14 is a flow diagram for illustrating an example of the process for succinic-acid production according to an embodiment.

(Crystallizer)

The crystallizer to be used in the invention is not particularly limited in the structure thereof so long as the crystallizer is a vessel equipped with a stirrer. Although a vessel which has a usually known stirrer can be used, a cylindrical vessel having a bottom is preferred. It is preferred to dispose baffles in the tank in order to efficiently shear the slurry. Furthermore, it is also possible to use a vessel which has a cylindrical guide, e.g., a guide called draft tube, in order to regulate the flow within the crystallization tank.

The shape of the vessel is not particularly limited. However, from the standpoints of rendering the slurry more even in the apparatus and efficiently shearing the slurry, a vessel is usually used in which the ratio between the diameter and height of the vessel (L/D) is preferably 0.5-3, more preferably 0.7-2.5, especially preferably 1-2.

As the crystallization tank, use can be made of a reactor in which the composition of the succinic-acid-containing liquid present in the tank is equal to the composition of the succinic-acid-containing liquid which is being discharged therefrom, i.e., a complete stirring tank type reactor (hereinafter often abbreviated to CSTR type). Alternatively, a crystallizer having a classifying function, which is an extensively used crystallizer, or the like can be used. Here, an explanation is given on a double-propeller type crystallizer (hereinafter often abbreviated to DP type), which is an extensively used crystallizer, by reference to FIG. 13.

This DP type crystallizer 10 mainly has a tank 1 to which a liquid to be treated is fed, a draft tube 2 disposed in the tank 1, and rotating blades 3 and 4 disposed inside and outside the draft tube 2.

The tank 1 has: an upper part 1a, which has an approximately cylindrical shape; a middle part 1b, which has an approximately cylindrical shape having a larger diameter than the upper part 1a and in which the lower half of the upper part 1a has been encased; and a lower part 1c, which extends from the lower end of the middle part 1b. That portion of the upper part 1a which has been encased in the middle part 1b serves as a baffle plate 5. The lower part 1c is composed of a cone part, in which the diameter thereof decreases downward from the lower end of the middle part 1b, and a bottom part, which closes the lower end of the cone part. A raw-liquid feed port 1d and a slurry discharge port 1e have been disposed in the cone part of the lower part 1c, and a discharge port 1h has been disposed in the bottom part of the lower part 1c. A clarified-mother-liquor outlet if has been disposed in the middle part 1b, and a vapor outlet 1g has been disposed in a panel part which covers the upper end of the upper part 1a.

The upper end of the draft tube 2 is located above the upper end of the clarified-mother-liquor outlet 1f, and the lower end of the draft tube 2 is located at a height corresponding to the middle of the lower part 1c. This draft tube 2 is composed of an upper draft tube 2a and a lower draft tube 2b, and the rotating blades 3 and 4 have been disposed securely on the inner and outer circumferential surfaces of the upper draft tube 2a. A rotating shaft 6 has been securely disposed at the center of the inner rotating blades 3. The tank 1 has been configured so that the rotating blades 3 and 4 can be rotated, together with the upper draft tube 2a, by rotating the rotating shaft 6 by means of a motor 7. The rotating blades 3 and 4 have been disposed in the baffle plate 5.

However, the draft tube 2 may be divided into three portions, i.e., an upper part, a middle part, and a lower part, and rotating blades 3 and 4 may be disposed in the middle part, as shown in FIG. 14. Alternatively, a draft tube 2 having an integral structure may be employed.

During crystallization, the liquid level L is located above the upper end of the middle part 1b and above the upper end of the draft tube 2, and that portion of the upper part 1a which is located above the liquid level L serves as a vaporization chamber 8, as shown in FIG. 13(a).

An example of the main specifications of the DP type crystallizer 10 is as shown below.

Major dimension, inner diameter of (middle part 1b): Φ350
Capacity: 230 L
Rotation speed: 93-375 rpm
Power: 2.2 kW, 200 V
Material: SUS316

Incidentally, the configuration of the crystallizer should not be construed as being limited to the DP type crystallizer 10, and the crystallizers disclosed in JP-B-43-19851 and JP-A-2004-154618 may, for example, be used.

(Examples of Production by Vaporization Crystallization)
An example of succinic-acid production by vaporization crystallization is explained below by reference to FIG. 14.
(1) Raw Liquid
A succinic-acid-containing liquid having a given concentration is stored in a jacketed raw-material tank 20. The concentration of succinic acid usually is 10-50% by weight, although the concentration thereof depends on the temperature at which the succinic acid was dissolved. The temperature at which succinic acid is dissolved is not particularly limited so long as the succinic acid dissolves. However, the acid is dissolved usually at a temperature in the range of 30-90° C.
(2) Liquid Introduction into Crystallizer 10, etc.
The succinic-acid-containing liquid is discharged from the tank 20 by operating a raw-liquid feed pump $P_1$, and is fed to a crystallizer 10 after having been diluted by adding tap water thereto. The succinic-acid concentration of this diluted raw liquid is not particularly limited so long as the concentration does not cause precipitation in the crystallizer 10. For example, the concentration thereof is 5-40% by weight.

The feeding of the succinic-acid-containing liquid to the crystallizer 10 is conducted until the liquid level L in the crystallizer 10 comes to be above the upper end of the draft tube 2 as shown in FIG. 13(a). Thereafter, the rotating blades 3 and 4 are rotated at a given stirring rotation speed (e.g., 100-350 rpm). Thus, as shown in FIG. 13(a), the succinic-acid-containing liquid which has been fed into the draft tube 2 through the raw-liquid feed port 1d ascends by the action of the rotation force of the rotating blades 3, flows out through the upper end of the draft tube 2, subsequently descends, by the action of the rotation force of the rotating blades 4, between the draft tube 2 and the baffle plate 5, and flows again into the draft tube 2 through the lower end of the draft tube 2. Thus, the succinic-acid-containing liquid circulates through the inside and the outside of the draft tube 2.

According to need, a slurry circulation pump $P_2$ is operated to initiate external circulation of the succinic-acid-containing liquid. It is preferred that this pump $P_2$ should be a pump which breaks at least some of the succinic acid crystals that have separated out through crystallization, and examples thereof include centrifugal pumps for slurries. The flow rate is not particularly limited so long as the crystals flow evenly within the pipeline. Although the flow rate depends on the size of the crystals, the flow rate is set usually at 0.2-5 m/sec in terms of linear velocity. The discharge pressure usually is 0.01-0.5 MPa although determined by the pump, size of the pipeline, flow rate, etc. A coolant may be passed through a slurry heat exchanger 21 or no coolant may be passed therethrough. A heating medium may be passed therethrough.

(3) Reduction of Internal Pressure of Crystallizer 10 and Concentration

The internal pressure of the crystallizer 10 is gradually reduced to vaporize the solvent, thereby concentrating the succinic-acid-containing liquid and simultaneously lowering the liquid temperature by means of the latent heat of vaporization. Crystallization of succinic acid is thus initiated. The crystallization temperature is not particularly limited, and usually is 5-50° C. Here, excessively reduced pressures are undesirable because the solvent which has been vaporized is difficult to condense. Conversely, too high pressures result in too low a recovery of succinic acid and hence in impaired efficiency. In the case where the succinic-acid-containing liquid is externally circulated, concentration of the succinic-acid-containing liquid is accelerated by passing a heating medium through the slurry heat exchanger 21.

The vapor which has accumulated in the vaporization chamber 8 as a result of vaporization that accompanied the pressure reduction is discharged through a vapor outlet 1g. The vapor discharged is condensed in a condenser 22 and subjected to gas-liquid separation in a separator 23. The resultant solvent is stored in a tank 24. Meanwhile, the succinic-acid-containing liquid present in the tank 20 is fed, without being diluted, into the crystallizer 10 intermittently or continuously. This feeding is conducted at such a rate that the liquid level L in the tank 1 is kept above the upper end of the draft tube 2. For example, the feed rate is about 20-200 L/hr. The succinic-acid-containing liquid in the crystallizer 10 is concentrated in the manner described above.

(4) Discharge of Succinic Acid
After the succinic-acid-containing slurry in the crystallizer 10 has come to have a given slurry concentration (e.g., 20-40% by weight), the rate of feeding the succinic-acid-containing liquid into the crystallizer 10 from the tank 20 is changed according to need. The feed rate is, for example, about 20-200 L/hr. This feeding of the succinic-acid-containing liquid may be either intermittent feeding or continuous feeding. However, continuous feeding enables succinic acid to be produced more stably. It is therefore preferred that when the succinic-acid-containing liquid was intermittently fed in (3) above, the feeding should be changed to continuous feeding.

The slurry in the crystallizer 10 is discharged continuously or intermittently through a slurry discharge port 1h while regulating the liquid level L. It is preferred that the rate of discharging the slurry should be 20-200 L/hr, in particular, 30-150 L/hr. In the case of intermittent discharge, it is preferred that the frequency of slurry discharge should be about 5-30 minutes each, in particular, about 10-20 minutes each. In this operation, care should be taken to keep the liquid level L above the upper surface of the draft tube 2 within the crystallizer 10.

With respect to the discharge of the slurry, the slurry can be intermittently discharged through a crystallization tank bottom valve by means of a pressure difference to a slurry discharge tank regulated so as to have a lower pressure than the crystallization tank, or the slurry can be continuously discharged with a slurry pump. In the case where the slurry is circulated, some of the slurry which is being circulated can be discharged continuously or intermittently. A pump can be selected while taking account of the flow rate, lifting height, desired size of the succinic acid particles, etc.

Pumps are roughly classified as turbo-pumps in which an impeller is rotated at a high speed within the casing to apply energy to the liquid, positive-displacement pumps in which the liquid present in a given space volume is changed in volume by a reciprocating motion or rotary motion to apply energy to the liquid, special pumps, etc. Pumps are selected in accordance with purposes while taking account of the degree of breaking of succinic acid particles, besides flow rate and lifting height. For actively breaking the succinic acid particles with a pump, use is made of a turbo-pump in which energy is applied to the succinic-acid-containing liquid by means of the impeller that is rotating at a high speed. Conversely, in the case where breakage of the succinic acid particles is desired to be minimized, a positive-displacement pump or the like is used. It is desirable that a positive-displacement pump capable of minimizing the breaking of the succinic acid particles, such as, for example, a snake pump, should be used for discharging the slurry.

The slurry discharged is subjected to solid-liquid separation with a basket type centrifugal separator 23 to separate the slurry into a wet cake and a mother liquor. The wet cake recovered is dried in a vacuum dryer (not shown) (for example, at 80° C. and 50 Torr). Thus, succinic acid particles are produced.

Incidentally, a clarified mother liquor which is low in the content of succinic acid particles stagnates between the baffle plate 5 and the middle part 1b of the crystallization tank 1. This classified mother liquor may be discharged continuously or intermittently through a clarified-mother-liquor outlet 1f using a pump $P_3$. The clarified mother liquor discharged is stored in a jacketed clarified-mother-liquor tank 25 and is sent back to the jacketed raw-liquid tank 20 with a pump $P_4$ according to need.

Seed crystals of succinic acid may be introduced into the crystallizer 10. Thus, succinic acid particles having a particle size distribution which is narrow and imparts excellent handleability to the particles can be crystallized. It is preferred that the seed crystals should have a volume-average particle diameter of 200 μm or less, in particular, 50-150 μm. The amount of the seed crystals to be added is preferably 0.001-20% by weight, in particular, 0.01-10% by weight, in terms of the amount of succinic acid recovered outside the system.

Methods for adding the seed crystals are not particularly limited. For example, seed crystals of succinic acid may be introduced into the crystallizer 10 from a pot 26 for feeding seed-crystal slurry. In the case where the slurry circulation pump $P_2$ is operated to externally circulate the succinic-acid-containing liquid, use can be made of a method in which the succinic acid particles contained in the liquid being circulated are broken with the slurry circulation pump $P_2$ and the broken particles are caused to act as seed crystals. In this case, a coolant or a heating medium may be passed through the slurry heat exchanger 21, or no medium may be passed therethrough. In the case where neither a coolant nor a heating medium is passed, the succinic-acid-containing liquid may be passed through a by-pass line (not shown) for the slurry heat exchanger 21.

The slurry circulation pump to be used here can be selected from pumps roughly classified as turbo-pumps in which an impeller is rotated at a high speed within the casing to apply energy to the liquid, positive-displacement pumps in which the liquid present in a given space volume is changed in volume by a reciprocating motion or rotary motion to apply energy to the liquid, special pumps, etc., in accordance with purposes while taking account of the degree of breaking of succinic acid particles, besides flow rate and lifting height. For actively breaking the succinic acid particles with a pump, it is desirable to use a turbo-pump in which energy is applied to the succinic-acid-containing liquid by means of the impeller that is rotating at a high speed. Conversely, in the case where breakage of the succinic acid particles is desired to be minimized, it is desirable to use a positive-displacement pump or the like.

The turbo-pumps for actively breaking the succinic acid particles by means of an impeller that is rotating at a high speed are further classified as centrifugal pumps in which the succinic-acid-containing liquid that is being discharged from the impeller is located mainly in a plane which is perpendicular to the main shaft, mixed-flow pumps in which the succinic-acid-containing liquid that is being discharged from the impeller is located in a conical surface, the axis of which is the same as the axis of the main shaft, and axial-flow pumps in which the succinic-acid-containing liquid that is being discharged from the impeller is located in a cylindrical surface which is coaxial with the main shaft. The kind of pump is suitably selected in accordance with applications while taking account of not only the flow rate and lifting height but also the degree of breaking of succinic acid particles. In the case where the succinic acid particles are desired to be broken especially efficiently, it is usually desirable to select a centrifugal pump. The centrifugal pumps and the mixed-flow pumps can be further classified by blade shape, i.e., whether or not an impeller skirt is present, as open impellers, closed impellers, etc. From the standpoint of the effect of breaking succinic acid particles, closed impellers are thought to be efficient. However, open impellers are usually employed because there is a possibility that clogging might occur within the pumps when a slurry is handled.

(Example of Cooling Crystallization Method)

Figure 15:
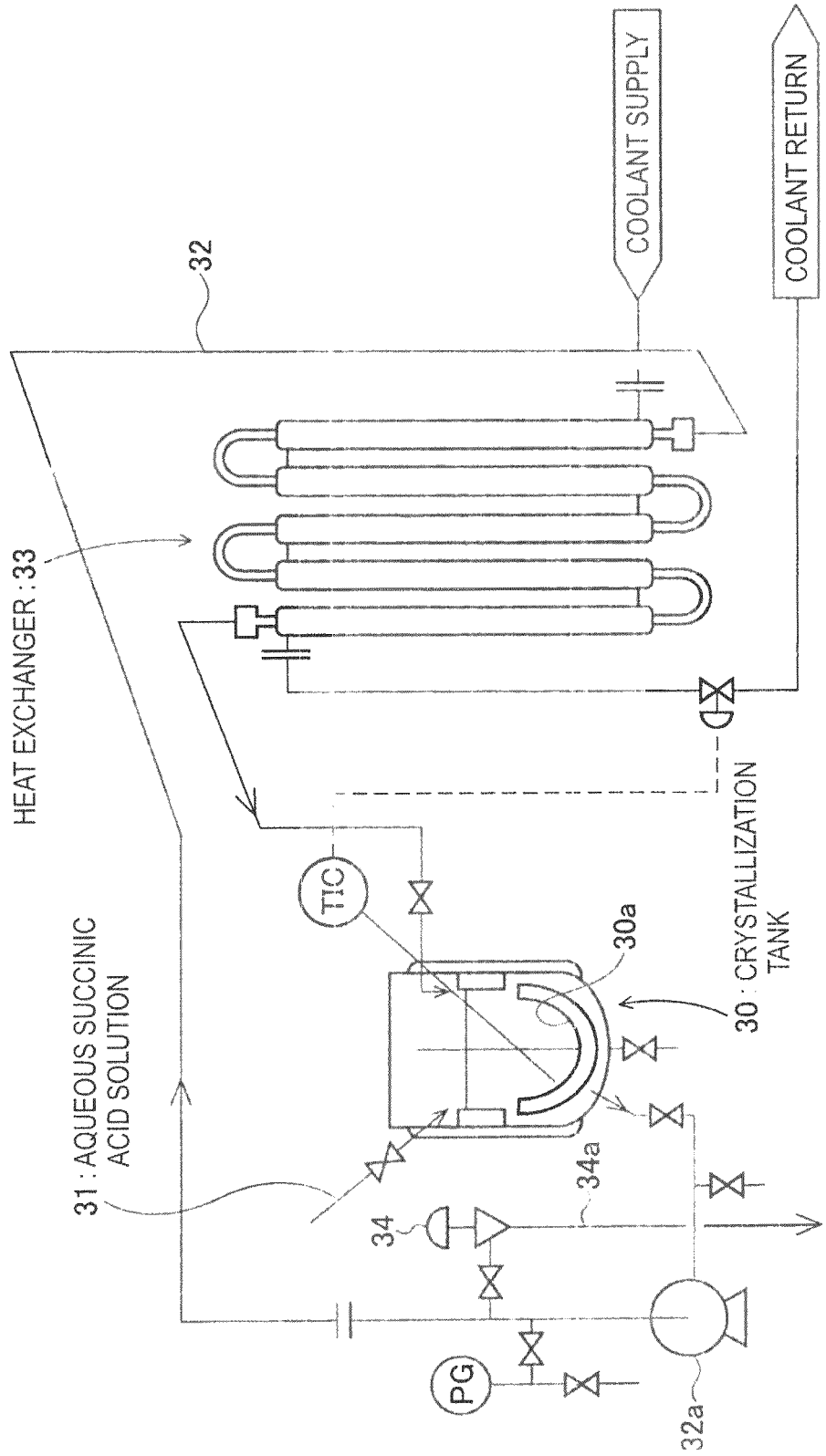
FIG. 15 is a flow diagram for illustrating a process for producing succinic acid according to another embodiment.

FIG. 15 is a flow diagram which illustrates an example of the cooling crystallization method. The specifications of the crystallizer shown in this example include: major dimension, Φ350; capacity, 63 L; stirring rotation speed, 10-120 rpm; power, 0.75 kW (200V); and material, SUS316 (JIS) stainless steel. In this example also, a succinic-acid-containing liquid having a given concentration (e.g., 10-50% by weight) and a given temperature (e.g., 30-90° C.) is stored in a jacketed raw-material tank (not shown).

This succinic-acid-containing liquid is fed in a given amount (e.g., 10-50 L) into a crystallization tank 30 through a raw-liquid feed pipeline 31. Subsequently, the contents begin to be stirred with a stirrer 30a at a given stirring rotation speed (e.g., 10-100 rpm) and, simultaneously therewith, the succinic-acid-containing liquid present in the crystallization tank 30 is circulated to a heat exchanger 33 through a circulation pipeline 32 equipped with a pump 32a. The rate of this circulation is, for example, about 0.5-5 m³/hr.

Subsequently, the flow rate of the coolant of the heat exchanger 33 is regulated using a temperature controller (TIC) to thereby lower the temperature of the liquid present in the crystallization tank 30 to a given temperature (e.g., 10-40° C.) over a given period (e.g., 1-5 hours). Thereafter, the temperature of the liquid in the crystallization tank 30 is kept at that given temperature to age the liquid for a given period. This aging period preferably is about 1-5 hours.

Subsequently, the succinic-acid-containing liquid is fed intermittently or continuously through the raw-liquid feed pipeline 31 and, simultaneously therewith, the slurry in the crystallization tank 30 is discharged intermittently or continuously while regulating the liquid level. For example, a discharge line 34a equipped with an electromagnetic valve 34 is disposed somewhere in the circulation pipeline 32 beforehand, and the electromagnetic valve 34 is opened at a given frequency by means of timer control to thereby discharge the slurry present in the crystallization tank 30 while regulating the liquid level. The rate of the feeding through the raw-liquid feed pipeline 31 is preferably about 10-100 L/hr, and the given frequency at which the slurry is discharged through the discharge line 34a is preferably about 5-30 minutes each.

The slurry discharged is subjected to solid-liquid separation with a basket type centrifugal separator and separated into a wet cake and a mother liquor, as in the case of FIG. 14. The wet cake recovered is dried in a vacuum dryer. Thus, succinic acid particles are produced.

EXAMPLES

The invention will be explained below by reference to Examples, but the invention should not be construed as being limited by the following Examples.

<Determination of Particle Diameter Distribution>

The particle diameter distribution of succinic acid obtained was determined by sieving the succinic acid by a method according to JIS Z8815 using standard wire sieves as provided for in JIS Z8801, which had an inner diameter of 200 mm, a depth of 45 mm, and opening sizes of 850 μm, 710 μm, 500 μm, 300 μm, and 150 μm, and further using a receiving pan and a lid. The sieving was conducted by shaking the sieves for 15 minutes using a rotating and tapping sieve shaker (F2-0003 type S-2, manufactured by Teraoka Corp.) having an oscillation frequency of 300 rpm and a hammering frequency of 150 strikes per minute.

For calculating a median diameter (hereinafter often referred to as d50), the particle diameter was plotted as abscissa (logarismic) and the minus-sieve content by weight was plotted as ordinate. The particle diameter corresponding to a minus-sieve content by weight of 50% was calculated by interpolation. In the same manner, the diameter corresponding to a minus-sieve content by weight of 20% (hereinafter often referred to as d20) and the diameter corresponding to a minus-sieve content by weight of 80% (hereinafter often referred to as d80) were calculated.

<Determination of Amounts of Succinic Acid and Fumaric Acid>
Column: ULTRON PS-80H, manufactured by Shinwa Chemical Industries Ltd.; 8.0 mm (I.D.)×30 cm
Eluent: water (containing perchloric acid) (1.8 mL of 60% aqueous perchloric acid solution/1 L of $H_2O$)
Temperature: 60° C.

<Determination of Amount of Ammonium Ions>
Quantitative analysis for ammonium ions in the Examples was made by ion chromatography under the following conditions.
Column: GL-IC-C75 (4.6 mm (I.D.)×150 mm)
Eluent: 3.5 mmol/L sulfuric acid
Column temperature: 40° C.

<Examination of Succinic Acid Crystals>
The succinic acid crystals obtained by the Examples were examined and photographed using digital microscope VH-8000, manufactured by Keyence Corp.

<Crystallization Tank>
In the Examples, either a jacketed separable flask made of glass and having a capacity of 1 L or 7 L or a stirring tank made of stainless steel and having a capacity of 63 L or 230 L was used as a crystallization tank. The power required for stirring in the crystallization tank having a capacity of 1 L or 7 L was measured in accordance with the following method.

<Measurement of Power Required for Stirring>
The power required for stirring in the crystallization tank having a capacity of 1 L or 7 L was measured in the following manner. The stirring blades were connected to an agitator equipped with a torque converter and capable of torque measurement (Three-One Motor BL600Te, manufactured by Shinto Scientific Co., Ltd.), and the contents were stirred while continuously measuring the torque. The torque was continuously inputted into a data logger (GL800, manufactured by Graphtec Corp.) at intervals of 20 seconds throughout the crystallization operation, and the Pv was calculated from the torque T using the following equation.

$Pv = T \times (2n\pi/60)/V$

Pv: power required for stirring per unit volume [kW/m³]
T: stirring torque [N·m]
n: stirring rotation speed [rpm]
V: volume of succinic-acid-containing liquid [m³]

<Production of Polyester and Evaluation of the Polymer>
[Preparation of Polycondensation Catalyst]

Into a 500-cm³ eggplant type flask made of glass and equipped with a stirrer was introduced 62.0 g of magnesium acetate tetrahydrate. Thereto was added 250 g of anhydrous ethanol (purity, 99% by weight or higher), followed by 35.8 g of ethyl acid phosphate (monoester/diester mixing ratio by weight, 45:55). The contents were stirred at 23° C. At 15 minutes thereafter, it was ascertained that the magnesium acetate had dissolved completely. Thereafter, 75.0 g of tetra-n-butyl titanate was added. Stirring was continued for further 10 minutes to obtain a homogenous mixture solution. This mixture solution was transferred to a 1,000-cm³ eggplant type flask, and the solution was concentrated at a reduced pressure in a 60° C. oil bath using an evaporator. At 1 hour thereafter, most of the ethanol had been distilled off and a translucent viscous liquid remained.

The temperature of the oil bath was further elevated to 80° C., and the concentration was further performed at a reduced pressure of 5 Torr. The viscous liquid gradually became powdery from the surface thereof, and wholly changed into a powder at two hours thereafter. Subsequently, the pressure was returned to ordinary pressure using nitrogen, and the contents were cooled to room temperature. Thus, 108 g of a light-yellow powder was obtained. The catalyst obtained gave the following data on analysis for metallic elements: titanium atom content, 10.3% by weight; magnesium atom content, 6.8% by weight; phosphorus atom content, 7.8% by weight; T/P molar ratio, 0.77; and M/P molar ratio, 1.0. Furthermore, the powdery catalyst was dissolved in 1,4-butanediol to prepare a solution so that the solution had a titanium atom concentration of 34,000 ppm.

[Production of Aliphatic Polyester]

Into a reaction vessel equipped with a stirrer, nitrogen introduction port, heater, thermometer, and evacuation port for pressure reduction were introduced 100 parts by weight of succinic acid, 99.2 parts by weight of industrial-grade 1,4-butanediol manufactured by Mitsubishi Chemical Corp., and 0.38 parts by weight of malic acid (total malic-acid amount, 0.33 mol % based on the succinic acid) as starting materials. The atmosphere in the system was converted to a nitrogen atmosphere by nitrogen-pressure reduction displacement.

Subsequently, the mixture in the system was heated to 230° C. over 1 hour and reacted at this temperature for 1 hour, while stirring the mixture. Thereafter, the catalyst solution was added thereto in such an amount that the amount of titanium atoms was 50 ppm of the polyester to be obtained. The reaction temperature was gradually elevated to 250° C. and, simultaneously therewith, the pressure was reduced to $0.06 \times 10^3$ Pa over 2 hours. The mixture was further reacted for 2.5 hours at this degree of vacuum to complete the polymerization. Thus, a polyester was obtained.

[Evaluation of the Polymer]

Yellowness (Hereinafter Often Referred to as YI)

The YI of the polyester obtained was determined in the following manner. In accordance with the method provided for in JIS K7105, Color meter ZE-6000, manufactured by Nippon Denshoku Kogyo K.K., was used, and a chip of the polymer was placed in the cell and examined four times by the reflection method. The average value thereof was taken as the YI.

Reduced Viscosity of the Polyester

The polyester obtained was dissolved in phenol/tetrachloroethane (1/1 (by mass) mixed liquid) so as to result in a concentration of 0.5 g/dL, and the time t (sec) required for the solution to fall through a viscometer tube in a 30° C. thermostatic bath was measured. The time to (sec) required for the solvent only to fall therethrough was also measured. The reduced viscosity $\eta_{sp}/C$ ($=(t-t_0)/t_0 \cdot C$) at 30° C. was calculated (C is the concentration of the solution).

Amount of Terminal Carboxyl Groups in the Polyester

The amount is a value obtained by dissolving the obtained polyester in benzyl alcohol and titrating the solution with 0.1-N NaOH. The amount is given in terms of the equivalent amount of carboxyl groups per $1 \times 10^6$ g.

<Production of Succinic-Acid-Containing Liquid (Crystallization Feed Liquid)>

Production of Pyruvate Carboxylase (PC)-Enhanced Strain (A) Extraction of *Brevibacterium flavum* MJ233 Strain Genom DNA

*Brevibacterium flavum* MJ233 was deposited, under accession No. FERM P-3068, at the National Institute of Bioscience and Human-Technology, Agency of Industrial Science and Technology, Ministry of International Trade and Industry (currently, International Patent Organism Depositary, National Institute of Advanced Industrial Science and Technology) (Central 6, 1-1, Higashi 1-chome, Tsukuba-shi, Ibaraki-ken, 305-8566, Japan) on Apr. 28, 1975, and was transferred to international deposition under Budapest Treaty on May 1, 1981 and received accession No. FERM BP-1497. A strain of *Brevibacterium flavum* MJ233 was cultured, to the late stage of the logarithmic phase, in 10 mL of culture medium A [2 g of urea, 7 g of $(NH_4)_2SO_4$, 0.5 g of $KH_2PO_4$, 0.5 g of $K_2HPO_4$, 0.5 g of $MgSO_4 \cdot 7H_2O$, 6 mg of $FeSO_4 \cdot 7H_2O$, 6 mg of $MnSO_4 \cdot 4-5H_2O$, 200 μg of biotin, 100 μg of thiamine, 1 g of yeast extract, 1 g of Casamino acid, and 20 g of glucose, all dissolved in 1 L of distilled water]. The cells were collected by centrifugal separation (10,000 g, 5 minutes). The cells obtained were suspended in 0.15 mL of a 10-mM NaCl/20-mM Tris buffer (pH 8.0)/1-mM EDTA·2Na solution containing lysozyme in a concentration of 10 mg/mL.

Subsequently, proteinase K was added to the suspension to a final concentration of 100 μg/mL, and this suspension was held at 37° C. for 1 hour. Furthermore, sodium dodecyl sulfate was added thereto to a final concentration of 0.5%, and this suspension was held at 50° C. for 6 hours to cause bacteriolysis. To the liquid which had undergone bacteriolysis was added the same amount of a phenol/chloroform solution. This mixture was gently shaken at room temperature for 10 minutes and then wholly subjected to centrifugal separation (5,000 G; 20 minutes; 10-12° C.). The supernatant fraction was taken out, and sodium acetate was added thereto so as to result in a concentration of 0.3 M. Thereafter, a 2-fold amount of ethanol was added to and mixed with the fraction. A precipitate was recovered through centrifugal separation (15,000 G, 2 minutes), washed with 70% ethanol, and then air-dried. To the DNA obtained was added 5 mL of a solution of 10-mM Tris buffer (pH 7.5)/1-mM EDTA·2Na. The resultant mixture was allowed to stand still at 4° C. overnight and used as a template DNA for PCR later.

(B) Construction of Plasmid for PC Gene Promoter Substitution

DNA fragments were acquired from the N-end regions of a pyruvate carboxylase gene derived from a strain of *Brevibacterium flavum* MJ233, by PCR using as a template the DNA prepared in (A) above and using synthetic DNAs (sequence No. 1 and sequence No. 2) designed on the basis of the sequence of that gene of a *Corynebacterium glutamicum* ATCC 13032 strain (GenBank Database Accession No. BA000036, Cg10689), the whole genom sequence of which has been reported. Incidentally, the DNA of sequence No. 1 was a DNA in which the 5'-end had been phosphorylated.

Reaction mixture composition: 1 μL of the template DNA, 0.2 μL of Pfx DNA polymerase (manufactured by Invitrogen Corp.), the attached buffer (×1 concentration), 0.3 μM of each primer, 1 mM of $MgSO_4$, and 0.25 μM of dNTPs were mixed together, and the total amount was adjusted to 20 μL.

Reaction temperature conditions: DNA thermal cycler PTC-200 (manufactured by MJ Research) was used to repeat a cycle 35 times, the cycle being composed of holding at 94° C. for 20 seconds, holding at 60° C. for 20 seconds, and holding at 72° C. for 1 minute. However, the 94° C.-holding in the first cycle was conducted for 1 minute and 20 seconds, and the 72° C.-holding in the final cycle was conducted for 4 minutes.

The amplification product was ascertained by subjecting the reaction mixture to separation by gel electrophoresis using 0.75% agarose (SeaKem GTG agarose; manufactured by FMC BioProducts) and then to visualization by staining with ethidium bromide. As a result, about 0.9 kb of fragments were detected. The desired DNA fragments were recovered from the gel using QIAQuick Gel Extraction Kit (manufactured by QIAGEN), and these fragments were used as PC gene N-end fragments.

On the other hand, TZ4 promoter fragments which were derived from a strain of *Brevibacterium flavum* MJ233 and constitutively highly showed expression were prepared by PCR using plasmid pMJPC1 (JP-A-2005-95169) as a template and using the synthetic DNAs described under sequence No. 3 and sequence No. 4. Incidentally, the DNA of sequence No. 4 was a DNA in which the 5'-end had been phosphorylated.

Reaction mixture composition: 1 μL of the template DNA, 0.2 μL of Pfx DNA polymerase (manufactured by Invitrogen Corp.), the attached buffer (×1 concentration), 0.3 μM of each primer, 1 mM of $MgSO_4$, and 0.25 μM of dNTPs were mixed together, and the total amount was adjusted to 20 μL.

Reaction temperature conditions: DNA thermal cycler PTC-200 (manufactured by MJ Research) was used to repeat a cycle 25 times, the cycle being composed of holding at 94° C. for 20 seconds, holding at 60° C. for 20 seconds, and holding at 72° C. for 30 seconds. However, the 94° C.-holding in the first cycle was conducted for 1 minute and 20 seconds, and the 72° C.-holding in the final cycle was conducted for 3 minutes.

The amplification product was ascertained by subjecting the reaction mixture to separation by gel electrophoresis using 1.0% agarose (SeaKem GTG agarose; manufactured by FMC BioProducts) and then to visualization by staining with ethidium bromide. As a result, about 0.5 kb of fragments were detected. The desired DNA fragments were recovered from the gel using QIAQuick Gel Extraction Kit (manufactured by QIAGEN), and these fragments were used as TZ4 promoter fragments.

The PC gene N-end fragments and TZ4 promoter fragments prepared above were mixed together and ligated using Ligation Kit ver. 2 (manufactured by Takara Shuzo Co., Ltd.). Thereafter, the ligated fragments were cleaved with restriction enzyme Pst I and separated by gel electrophoresis using 1.0% agarose (SeaKem GTG agarose; manufactured by FMC BioProducts). About 1.0 kb of DNA fragments were recovered using QIAQuick Gel Extraction Kit (manufactured by QIAGEN), and these fragments were used as TZ4 promoter// PC gene N-end fragments. These DNA fragments were mixed with a DNA prepared by cleaving *Escherichia coli* plasmid pHSG299 (manufactured by Takara Shuzo Co., Ltd.) with Pst I, and were ligated therewith using Ligation Kit ver. 2 (manufactured by Takara Shuzo Co., Ltd.).

The plasmid DNA obtained was used to transform *Escherichia coli* (DH5α strain). The recombinant *Escherichia coli* thus obtained was applied to an LB agar medium containing 50 μg/mL kanamycin and 50 μg/mL X-Gal. The clone which formed a white colony on the medium was cultured in a liquid in an ordinary way. Thereafter, the plasmid DNA was purified. The plasmid DNA obtained was cleaved with restriction enzyme Pst I. As a result, about 1.0 kb of insert fragments were observed. These fragments were named pMJP C17.1.

DNA fragments were acquired from the 5'-upstream regions of a pyruvate carboxylase gene derived from a strain of *Brevibacterium flavum* MJ233, by PCR using as a template the DNA prepared in (A) above and using synthetic DNAs (sequence No. 5 and sequence No. 6) designed on the basis of the sequence of that gene of a *Corynebacterium glutamicum* ATCC 13032 strain (GenBank Database Accession No. BA000036), the whole genom sequence of which has been reported.

Reaction mixture composition: 1 μL of the template DNA, 0.2 μL of Pfx DNA polymerase (manufactured by Invitrogen Corp.), the attached buffer (×1 concentration), 0.3 μM of each primer, 1 mM of $MgSO_4$, and 0.25 μM of dNTPs were mixed together, and the total amount was adjusted to 20 μL.

Reaction temperature conditions: DNA thermal cycler PTC-200 (manufactured by MJ Research) was used to repeat a cycle 35 times, the cycle being composed of holding at 94° C. for 20 seconds, holding at 60° C. for 20 seconds, and holding at 72° C. for 30 seconds. However, the 94° C.-holding in the first cycle was conducted for 1 minute and 20 seconds, and the 72° C.-holding in the final cycle was conducted for 5 minutes.

The amplification product was ascertained by subjecting the reaction mixture to separation by gel electrophoresis using 1.0% agarose (SeaKem GTG agarose; manufactured by FMC BioProducts) and then to visualization by staining with ethidium bromide. As a result, about 0.7 kb of fragments were detected. The desired DNA fragments were recovered from the gel using QIAQuick Gel Extraction Kit (manufactured by QIAGEN).

The 5'-ends of the DNA fragments recovered were phosphorylated with T4 Polynucleotide Kinase (manufactured by Takara Shuzo Co., Ltd.). Thereafter, the DNA fragments were ligated to the Sma I site of *Escherichia coli* vector pUC119 (manufactured by Takara Shuzo Co., Ltd.) using Ligation Kit ver. 2 (manufactured by Takara Shuzo Co., Ltd.). The plasmid DNA obtained was used to transform *Escherichia coli* (DH5α strain). The recombinant *Escherichia coli* thus obtained was applied to an LB agar medium containing 50 μg/mL ampicillin and 50 μg/mL X-Gal. The clone which formed a white colony on the medium was cultured in a liquid in an ordinary way. Thereafter, the plasmid DNA was purified.

The plasmid DNA obtained was subjected to a PCR reaction in which synthetic DNAs represented by sequence No. 7 and sequence No. 6 were used as primers. Reaction mixture composition: 1 ng of the plasmid, 0.2 μL of Ex-Taq DNA polymerase (manufactured by Takara Shuzo Co., Ltd.), the attached buffer (×1 concentration), 0.2 μM of each primer, and 0.25 μM of dNTPs were mixed together, and the total amount was adjusted to 20 μL. Reaction temperature conditions: DNA thermal cycler PTC-200 (manufactured by MJ Research) was used to repeat a cycle 20 times, the cycle being composed of holding at 94° C. for 20 seconds, holding at 60° C. for 20 seconds, and holding at 72° C. for 50 seconds. However, the 94° C.-holding in the first cycle was conducted for 1 minute and 20 seconds, and the 72° C.-holding in the final cycle was conducted for 5 minutes. Whether insert DNA fragments were present or not was thus ascertained. As a result, a plasmid which gave about 0.7 kb of an amplification product was selected and named pMJPC5.1.

Subsequently, the pMJPC17.1 and the pMJPC5.1 each were cleaved with restriction enzyme Xba I, and then mixed together and ligated using Ligation Kit ver. 2 (manufactured by Takara Shuzo Co., Ltd.). The ligated fragments were cleaved with restriction enzyme Sac I and restriction enzyme Sph I, and the resultant DNA fragments were separated by gel electrophoresis using 0.75% agarose (SeaKem GTG agarose; manufactured by FMC BioProducts). About 1.75 kb of DNA fragments were recovered using QIAQuick Gel Extraction Kit (manufactured by QIAGEN). DNA fragments obtained by inserting a TZ4 promoter between the 5'-upstream region and the N-end region of the PC gene were mixed with a DNA prepared by cleaving plasmid pKMB1 containing a sacB gene (JP-A-2005-95169) with Sac I and Sph I and were ligated thereto using Ligation Kit ver. 2 (manufactured by Takara Shuzo Co., Ltd.).

The plasmid DNA obtained was used to transform *Escherichia coli* (DH5α strain). The recombinant *Escherichia coli* thus obtained was applied to an LB agar medium containing 50 μg/mL kanamycin and 50 μg/mL X-Gal. The clone which formed a white colony on the medium was cultured in a liquid in an ordinary way. Thereafter, the plasmid DNA was purified. The plasmid DNA obtained was cleaved with restriction enzymes Sac I and Sph I. As a result, about 1.75 kb of insert fragments were observed. These fragments were named pMJPC 17.2.

(C) Production of PC-Enhanced Strain

A plasmid DNA to be used for transforming *Brevibacterium flavum* MJ233/ΔLDH (lactate dehydrogenase gene disruption strain: JP-A-2005-95169) was reprepared from an *Escherichia coli* JM110 strain which had been transformed using the plasmid DNA of pMJPC17.2 by the calcium chloride method (*Journal of Molecular Biology*, 53, 159, 1970). The transformation of the *Brevibacterium flavum* MJ233/ΔLDH strain was conducted by the electric pulse method (*Res. Microbiol.*, Vol. 144, pp. 181-185, 1993). The transformant obtained was applied to an LBG agar medium [10 g of tripton, 5 g of yeast extract, 5 g of NaCl, 20 g of glucose, and 15 g of agar were dissolved in 1 L of distilled water] which contained kanamycin in a concentration of 25 µg/mL. The strain that grew on the medium was a plasmid in which pMJPC 17.2 was unable to be duplicated in the cells of the *Brevibacterium flavum* MJ233 strain. Consequently, homologous recombination should have occurred between the PC gene of the plasmid and the same gene present on the genome of the *Brevibacterium flavum* MJ233 strain and, as a result, a kanamycin-resistant gene and a sacB gene both derived from that plasmid should have been inserted into the genome.

Subsequently, the homologous recombinant strain was cultured in a liquid LBG medium containing kanamycin in a concentration of 25 µg/mL. A portion of this culture medium which corresponded to a number of cells of about 1,000,000 was applied to an LBG medium containing 10% sucrose. As a result, several tens of strains which were thought to have undergone second homologous recombination and resultant elimination of the sacB gene and hence become not sensitive to sucrose were obtained. The strains thus obtained include ones in which a TZ4 promoter derived from pMJPC 17.2 has been inserted upstream from the PC gene and ones which have returned to the wild type. Whether a PC gene is of the promoter-substituted type or the wild type can be easily ascertained by directly subjecting the cells obtained by liquid culture in an LBG medium to a PCR reaction and then to PC gene detection. When analyzed with a TZ4 promoter and primers (sequence No. 8 and sequence No. 9) for PCR amplification of PC genes, a PC gene of the promoter-substituted type should give a 678-bp DNA fragment.

The strains which had been rendered not sensitive to sucrose by the method described above were analyzed. As a result, a strain in which a TZ4 promoter had been inserted was selected and named *Brevibacterium flavum* MJ233/PC-4/ΔLDH.

(D) Determination of Pyruvate Carboxylase Enzyme Activity

The transformed strain obtained in (C) above, i.e., the *Brevibacterium flavum* MJ233/PC-4/ΔLDH strain, was cultured overnight in 100 mL of medium A containing 2% glucose and 25 mg/L kanamycin. The cells obtained were collected, rinsed with 50 mL of 50-mM potassium phosphate buffer (pH 7.5), and suspended again in 20 mL of a buffer having the same composition. This suspension was smashed with SONIFIER 350 (manufactured by BRANSON) and centrifuged, and the resultant supernatant was recovered as a cell-free extract.

The cell-free extract obtained was used and examined for pyruvate carboxylase activity. The enzyme activity was examined by reacting the extract at 25° C. in a reaction liquid containing 100-mM Tris/HCl buffer (pH 7.5), 0.1 mg/10 mL biotin, 5-mM magnesium chloride, 50-mM sodium hydrogen carbonate, 5-mM sodium pyruvate, 5-mM sodium adenosine triphosphate, 0.32-mM NADH, 20 units/1.5 mL malic acid dehydrogenase (manufactured by WAKO; derived from yeast), and the enzyme. The amount of the enzyme required for catalyzing an NADH decrease of 1 µmol per minute was expressed by 1 U. The cell-free extract which had been made to show enhanced pyruvate carboxylase expression had a specific activity of 0.1 U/mg-protein. Incidentally, cells obtained by likewise culturing an MJ233/ΔLDH strain, which was a parent strain, gave a value that was below the detection limit for this method for activity determination.

The *Brevibacterium flavum* MJ233/PC-4/ΔLDH strain was used below as an organic-acid-producing microorganism in culture for preparing cells and in a reaction for organic-acid production.

Preparation of Culture Medium Containing Succinic Acid Salt (Seed Culture)

Into a 500-mL Erlenmeyer flask was introduced 100 mL of a culture medium obtained by mixing 4 g of urea, 14 g of ammonium sulfate, 0.5 g of monopotassium phosphate, 0.5 g of dipotassium phosphate, 0.5 g of magnesium sulfate heptahydrate, 20 mg of ferrous sulfate heptahydrate, 20 mg of manganese sulfate hydrate, 200 µg of D-biotin, 200 µg of thiamine hydrochloride, 5 g of yeast extract, 5 g of Casamino acid, and 1,000 mL of distilled water. The culture medium was sterilized by heating at 120° C. for 20 minutes. This culture medium was cooled to room temperature, and 4 mL of 50% aqueous glucose solution which had been sterilized beforehand was added thereto. The *Brevibacterium flavum* MJ233/PC-4/ΔLDH constructed above was inoculated thereinto, and seed culture was conducted at 30° C. for 24 hours.

(Main Culture)

Into a 1-L fermenter was introduced 400 mL of a culture medium obtained by mixing 1.0 g of ammonium sulfate, 1.5 g of monopotassium phosphate, 1.5 g of dipotassium phosphate, 1.67 g of potassium chloride, 0.5 g of magnesium sulfate heptahydrate, 40 mg of ferrous sulfate heptahydrate, 40 mg of manganese sulfate hydrate, 1.0 mg of D-biotin, 1.0 mg of thiamine hydrochloride, 10 g of yeast extract, 1.0 g of an antifoaming agent (CE457, manufactured by Nippon Oil & Fats Co., Ltd.), and 1,000 mL of distilled water. The culture medium was sterilized by heating at 120° C. for 20 minutes. This culture medium was cooled to room temperature. Thereafter, 20 mL of 72% aqueous glucose solution which had been sterilized beforehand was added thereto. Twenty milliliters of the seed culture medium described above was added thereto, and the mixture was kept at 30° C. Main culture was conducted for 24 hours under the aeration and stirring conditions of 300 mL/min and 600 rpm, respectively, while keeping the pH above 7.0 using 9.3% ammonia water.

The dissolved-oxygen concentration began to decrease gradually from immediately after initiation of the culture and became substantially 0 at 4 hours after the culture initiation. At 15 hours after the culture initiation, the dissolved-oxygen concentration rose. Consequently, 380 µL of 72% aqueous glucose solution which had been sterilized beforehand was added thereto. As a result, the dissolved-oxygen concentration rapidly decreased again and became substantially 0. At about 13 minutes thereafter, an increase in dissolved-oxygen concentration was observed likewise. Consequently, 380 µL of 72% aqueous glucose solution which had been sterilized beforehand was added thereto to lower the dissolved-oxygen concentration again. Thereafter, the same increase was observed at intervals of about 13 minutes, and the dissolved-oxygen concentration was lowered each time in the same manner. After the culture was conducted for 24 hours, the value of OD660 was 87.3.

(Organic-Acid Production Culture)

Into a 500-mL Erlenmeyer flask was introduced a culture medium obtained by mixing 84.4 mg of monoammonium phosphate, 75.8 mg of diammonium phosphate, 149.1 mg of potassium chloride, 0.2 g of magnesium sulfate heptahydrate, 8 mg of ferrous sulfate heptahydrate, 8 mg of manganese sulfate hydrate, 80 µg of D-biotin, 80 µg of thiamine hydrochloride, and 200 mL of distilled water. The culture medium was sterilized by heating at 120° C. for 20 minutes. The culture medium was cooled to room temperature and then introduced into a 1-L jar fermenter. To 200 mL of this suspension were added 90 mL of the culture medium obtained by the main culture described above, 40 mL of a 72% glucose solution which had been sterilized beforehand, and 125 mL of distilled water. The ingredients were mixed together, and the mixture was kept at 35° C. A reaction for organic-acid production was conducted while stirring the mixture at 200 rpm and while keeping the pH at 7.6 using an aqueous solution obtained by mixing 154 g of ammonium carbonate, 239 mL of 28% ammonia water, and 650 mL of distilled water. At 21 hours after initiation of the reaction, the concentration of the succinic acid produced was 34.8 g/L and this fermentation broth contained a small amount of fumaric acid.

The succinic acid fermentation broth thus prepared was centrifuged (10,000 G, 10 minutes) to obtain an aqueous solution which contained the ammonium succinate obtained. Preparation of Succinic-Acid-Containing Flow Liquid (Crystallization Feed Liquid)

The aqueous ammonium succinate solution obtained by the culture was concentrated with heating at a reduced pressure. While the concentrated culture medium was being stirred, 47% sulfuric acid was dropped into the culture medium to adjust the pH of the solution to 2. Methyl ethyl ketone (hereinafter often abbreviated to MEK) was added as an organic solvent to the culture medium to which sulfuric acid had been added, the amount by volume of the MEK being equal to that of the culture medium, and the resultant mixture was stirred at 25° C. for about 30 minutes. The liquid thus obtained was allowed to stand still and then separated into an organic layer and an aqueous layer. MEK was added to the separated aqueous layer in an amount of one-half by volume the amount of the aqueous layer, and the resultant mixture was stirred at 25° C. for 30 minutes. This liquid was allowed to stand still and then separated into an organic layer and an aqueous layer in the same manner. The same operation was further repeated three times, and all the organic layers were put together. The resultant organic layer was analyzed by liquid chromatography (LC). As a result, it was found that 97.9% of the succinic acid which had been contained in the broth had been extracted and incorporated into the organic layer.

Subsequently, the organic layer obtained by extraction with MEK was concentrated by distilling off the MEK from the resultant MKE extract at 70° C. while regulating the degree of vacuum from 400 mmHg to 100 mmHg. Thereafter, the temperature of the solution obtained was lowered from 70° C. to 40° C. over 30 minutes, and this solution was then stirred at 40° C. for 1 hour. The crystals which had precipitated were taken out by filtration and then rinsed with cold water to obtain crude crystals. On the other hand, the filtrate was further cooled from 40° C. to 10° C. over 30 minutes and stirred at 10° C. for 1 hour. The crystals which had precipitated were taken out by filtration and rinsed with cold water to obtain crude crystals. These crude crystals obtained were evenly mixed with the crude crystals obtained first, and the mixture was subjected to the next step.

To the crude crystals obtained was added pure water in such an amount as to result in a liquid which contained 30% by weight the crude succinic acid. The crude crystals were dissolved at 80° C. Thereafter, powdery activated carbon (DIA-HOPE 8ED, manufactured by Calgon Mitsubishi Chemical Corp.) in an amount of 0.3% by weight based on the succinic acid. A treatment with the activated carbon was conducted for 3 hours using a thermostatic shaker kept at 80° C. Thereafter, the activated carbon was filtered off at 80° C.

Furthermore, the succinic-acid-containing liquid obtained was introduced into a 500-mL induction stirring autoclave made of SUS316, and was hydrotreated in the pressure of 5% Pd/C (Wako Catalog 326-81672; catalyst amount, 0.06% by weight based on the succinic acid) under the conditions of a hydrogen pressure of 0.8 MPa, a reaction temperature of 80° C., and a reaction time of 3 hours. As a result, the fumaric acid which had been contained in the crude succinic acid in an amount of 1.8% by weight based on the succinic acid was wholly induced to succinic acid. After completion of the reaction, the catalyst was filtered off. The succinic-acid-containing liquid thus obtained was subjected to the following Examples and Comparative Examples. This succinic-acid-containing liquid had a succinic-acid concentration of 32% by weight and an ammonium ion concentration of 30 ppm (94 ppm of the succinic acid). The 32% by weight aqueous succinic acid solution had a saturation temperature of 70° C. The succinic-acid-containing solution thus obtained was subjected to the following Examples and Comparative Examples.

Example 1-1

Five hundred milliliters (540 g) of the succinic-acid-containing liquid was introduced into a crystallizer, such as that shown in FIG. 1, which was constituted of a jacketed separable flask having an inner diameter of 86 mm that was equipped with four baffles having a width of 10 mm and with a stirrer that had four-paddle impellers which had been arranged in two stages and had a diameter of 50 mm and in which the blades each had a width of 15 mm and faced downward at 45°. The contents were kept at 80° C. by passing hot water through the jacket while stirring the contents at 500 rpm. Subsequently, the temperature of the water being passed through the jacket was lowered to 20° C. over 1 hour at a rate of 1° C./min, and the contents were thereafter kept being cooled for further 1 hour so that the internal temperature of the crystallization tank was kept at 20° C. After completion of the crystallization, the power Pv required for stirring per unit volume was calculated from the torque T. As a result, the Pv was found to be 1 kW/m$^3$.

Figure 2:
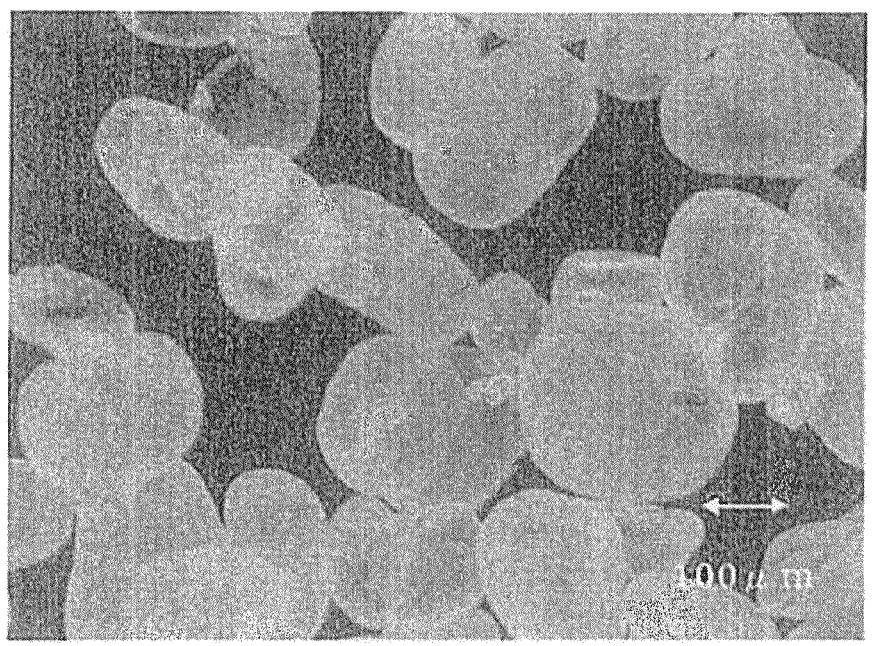
FIG. 2 is a photomicrograph of the crystals of succinic acid obtained in Example 1-1.

Thereafter, the succinic-acid slurry was filtered and thereby separated into 155 g of a wet succinic-acid cake and 380 g of a mother liquor. The wet succinic-acid cake obtained in an amount of 155 g was introduced into a 1-L beaker together with 700 g of pure water and suspension-washed therein, and the slurry was filtered. The wet cake obtained was vacuumed-dried at 70° C. for 12 hours to obtain succinic acid which was white and odorless. The crystals obtained were examined with a microscope. As a result, it was found that crystals having a smooth surface, as shown in FIG. 2, had been obtained. Furthermore, the succinic acid was examined for $NH_4^+$ ion content therein. As a result, the content thereof was found to be 0.2 ppm.

Example 1-2

Figure 3:
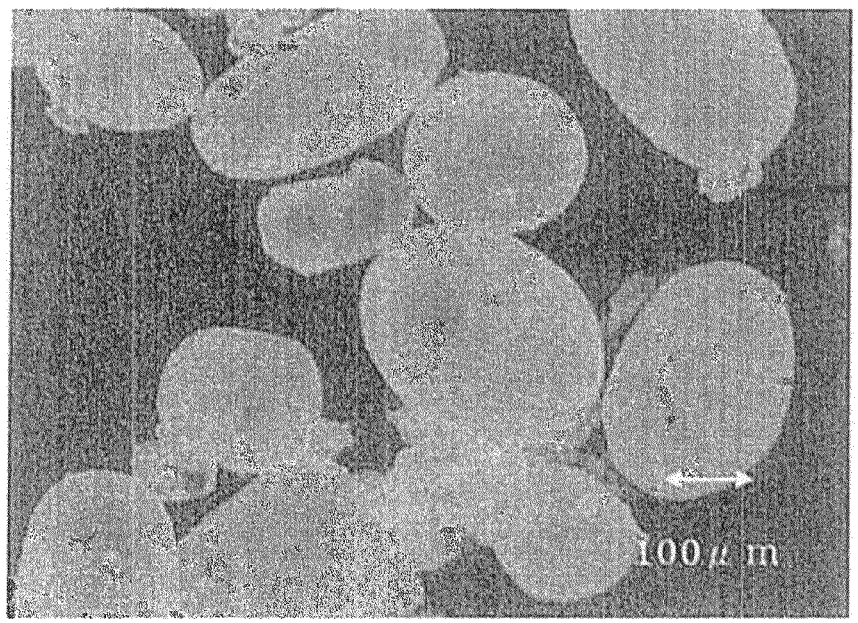
FIG. 3 is a photomicrograph of the crystals of succinic acid obtained in Example 1-2.

A crystallization operation was conducted in the same manner as in Example 1-1, except that the temperature of the water being passed through the jacked was lowered to 20° C. over 2.5 hours at a rate of 0.4° C./min and the contents were thereafter kept being cooled for further 1 hour so that the internal temperature of the crystallization tank was kept at 20° C. The power Pv required for stirring per unit volume was 1.0 kW/m$^3$. The crystals obtained were examined with a microscope. As a result, it was found that crystals having a smooth surface, as shown in FIG. 3, had been obtained. Furthermore, the succinic acid was examined for NH$_4^+$ ion content therein. As a result, the content thereof was found to be 0.2 ppm.

Example 1-3

Figure 4:
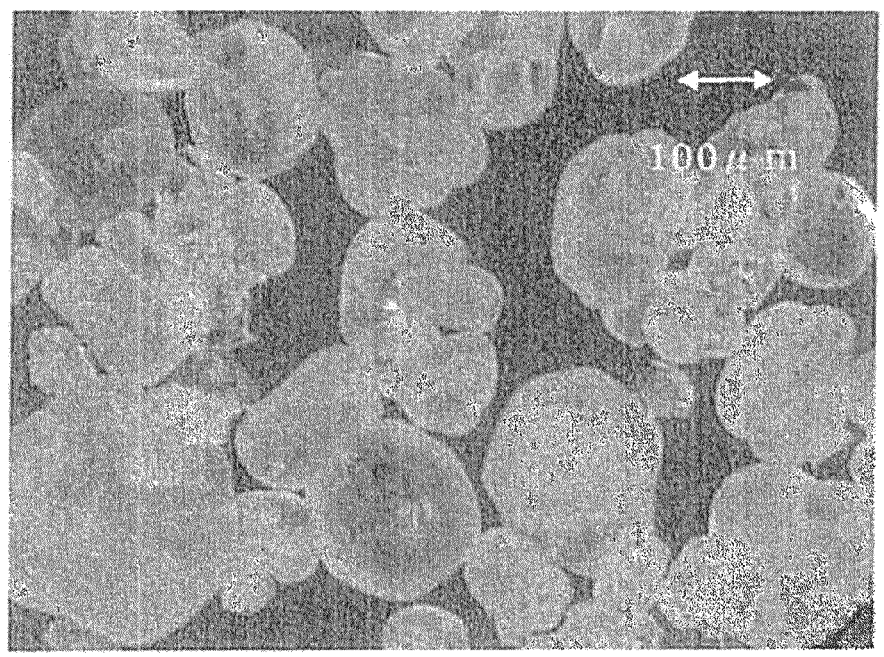
FIG. 4 is a photomicrograph of the crystals of succinic acid obtained in Example 1-3.

A crystallization operation was conducted in the same manner as in Example 1-1, except that the stirring rotation speed was changed to 400 rpm. The power Pv required for stirring per unit volume was 0.5 kW/m$^3$. The crystals obtained were examined with a microscope. As a result, it was found that crystals having a smooth surface, as shown in FIG. 4, had been obtained. Furthermore, the succinic acid was examined for NH$_4^+$ ion content therein. As a result, the content thereof was found to be 0.2 ppm.

Comparative Example 1-1

Figure 5:
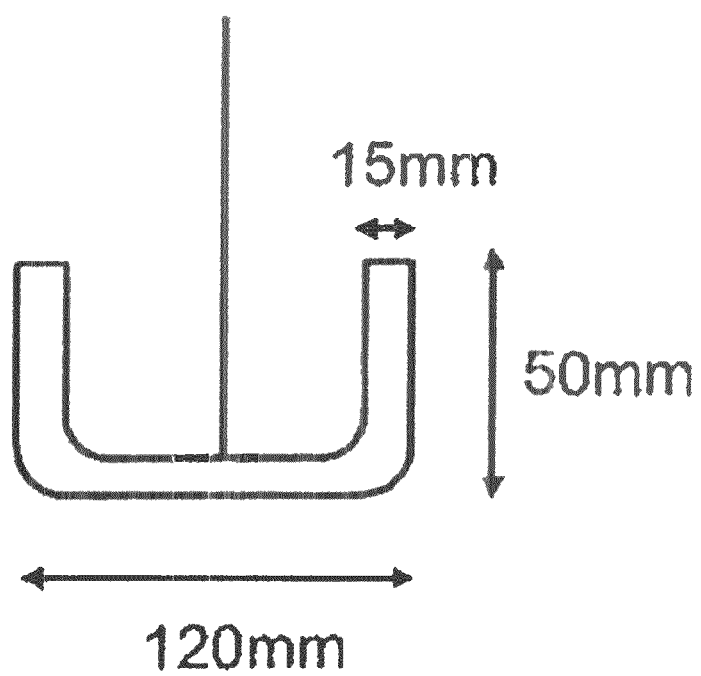
FIG. 5 is a drawing which shows the anchor blade used in Comparative Example 1-1.
Figure 6:
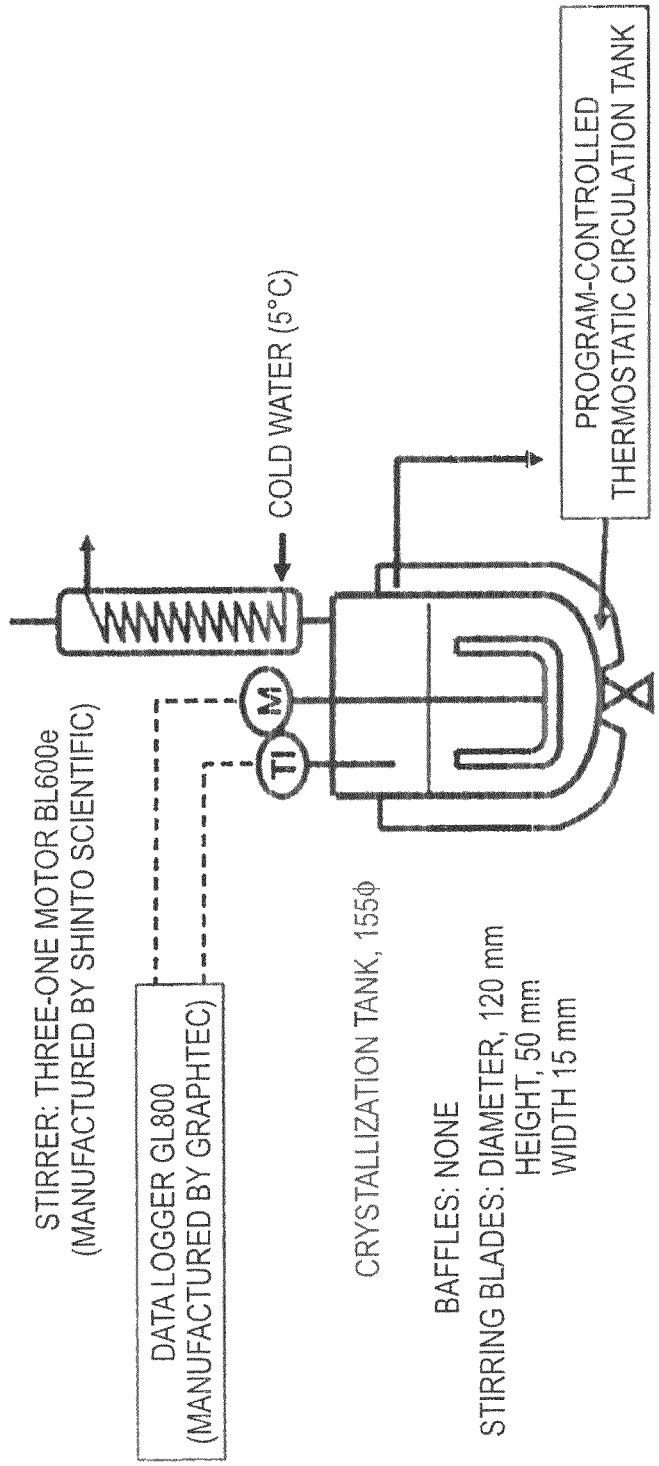
FIG. 6 is a drawing which shows the crystallizer used in Comparative Example 1-1.

Five liters (5,400 g) of the succinic-acid-containing liquid was introduced into a crystallizer, such as that shown in FIG. 6, which was constituted of a jacketed separable flask having an inner diameter of 150 mm that was equipped with a stirrer which had an anchor blade having a diameter of 120 mm, height of 50 mm, and width of 15 mm, such as that as shown in FIG. 5. The contents were kept at 80° C. by passing hot water through the jacket while stirring the contents at 300 rpm.

Figure 7:
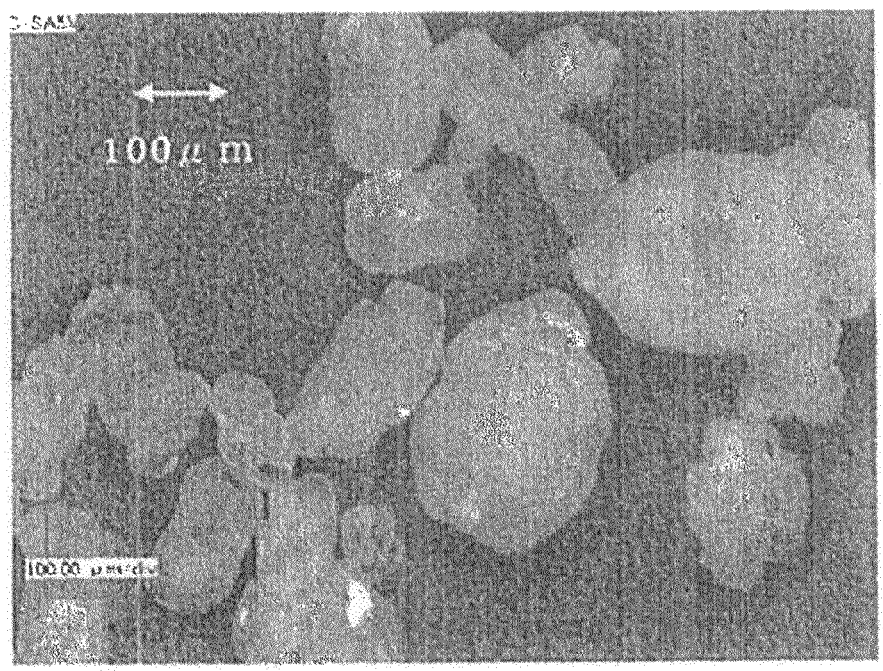
FIG. 7 is a photomicrograph of the crystals of succinic acid obtained in Comparative Example 1-1.

Thereafter, the temperature of the water being passed through the jacket was lowered to 20° C. over 2.5 hours at a rate of 0.4° C./min, and the contents were subsequently kept being cooled for further 1 hour so that the internal temperature of the crystallization tank was kept at 20° C. After completion of the crystallization, the power Pv per unit volume was calculated from the torque T. Furthermore, the average of the power Pv required for stirring during the crystallization operation was calculated and was found to be 0.3 kW/m$^3$. The succinic-acid slurry obtained by the crystallization was filtered and thereby separated into 1,500 g of a wet succinic-acid cake and 3,900 g of a mother liquor. The wet succinic-acid cake obtained in an amount of 1,500 g was introduced into a 10-L polyethylene vessel together with 7,000 g of pure water and suspension-washed therein, and the slurry was filtered. The wet cake obtained was vacuum-dried at 70° C. for 12 hours to obtain succinic acid which was white and odorless. The crystals obtained were examined with a microscope. As a result, it was found that the crystals each had many recesses and protrusions presumed to have been formed as a result of aggregating of several crystals, as shown in FIG. 7. The succinic acid was analyzed for NH$_4^+$ ion content therein. As a result, the content thereof was found to be 1.0 ppm.

Example 2-1

Figure 8:
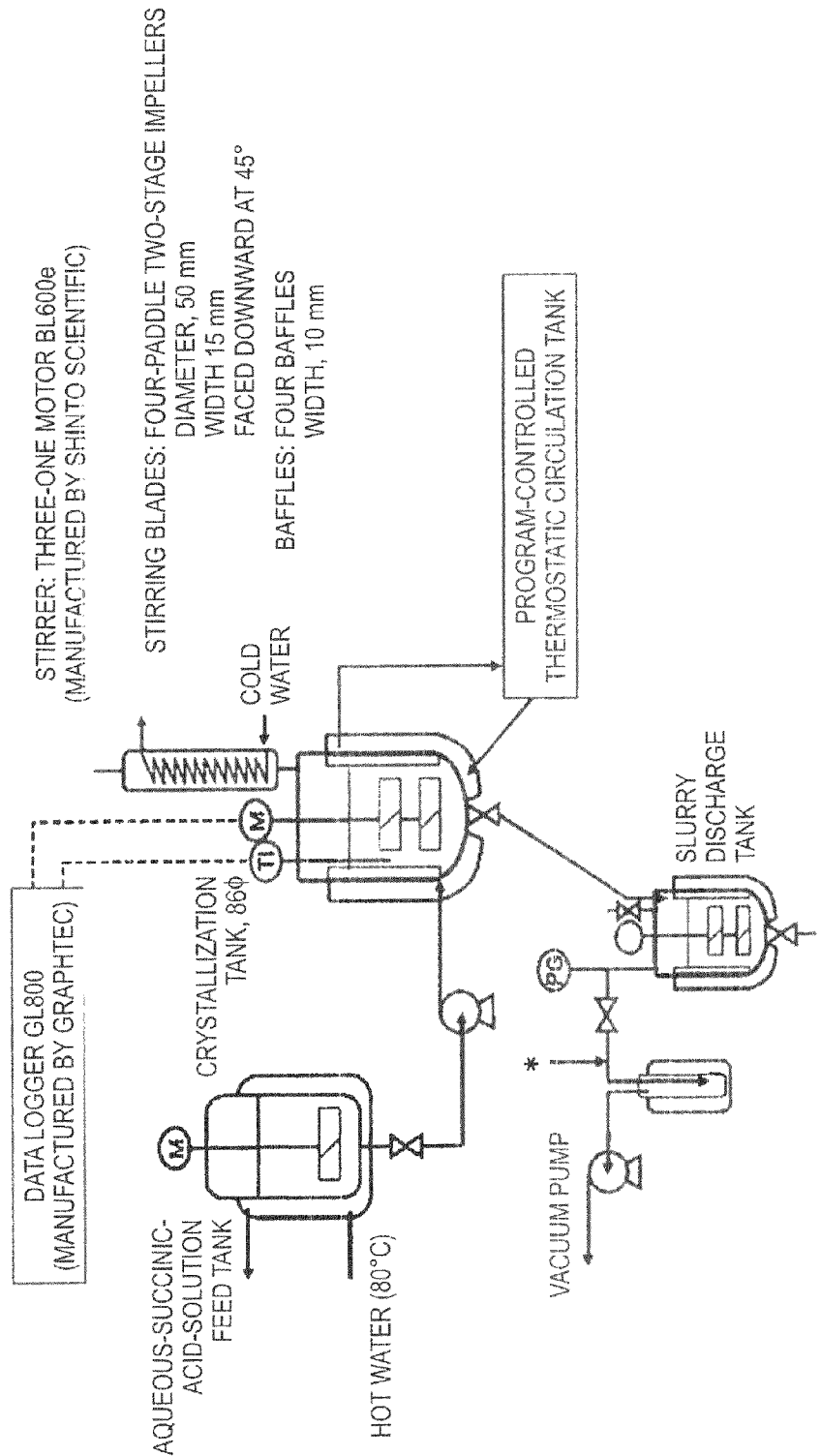
FIG. 8 is a drawing which shows the crystallizer used in Examples 2-1 and 2-2, Comparative Examples 2-1 and 2-2, Examples 3-1 to 3-3, and Comparative Examples 3-1 to 3-3.

The succinic-acid-containing liquid was fed to a crystallizer, such as that shown in FIG. 8, which was constituted of a jacketed separable flask having an inner diameter of 86 mm that was equipped with four baffles having a width of 10 mm and with a stirrer that had four-inclined-paddle impellers which had been arranged in two stages and had a diameter of 50 mm and in which the blades each had a width of 15 mm and faced downward at 45°. The succinic-acid-containing liquid was fed to the crystallizer so that the inside of the crystallizer did not become empty, and cooling crystallization was conducted.

Five hundred milliliters of the succinic-acid-containing liquid was introduced into the stirring tank in which 80° C. hot water was being passed through the jacket. The paddle impellers were rotated at 500 rpm to completely dissolve the succinic acid contained in the succinic-acid-containing liquid to bring the succinic-acid-containing liquid into a state in which no solid matter was observed.

After it was ascertained that the succinic acid had dissolved, the temperature of the hot water being supplied to the jacket was lowered to 20° C. over about 1 hour to lower the internal temperature of the crystallization tank to 20° C. After the internal temperature became 20° C., the contents were continuously stirred for further 1 hour while maintaining that temperature.

Thereafter, the succinic-acid-containing liquid was continuously fed at 250 mL/min while the temperature of the cold water being passed through the jacket was being regulated so that the internal temperature of the crystallization tank was able to be kept at 20° C. Simultaneously therewith, a slurry containing solid succinic acid was intermittently discharged to a slurry discharge tank at intervals of about 15 minutes so that the volume of the succinic-acid slurry in the crystallization tank was substantially constant. The succinic-acid-containing slurry discharged was filtered under vacuum and thereby separated into a wet succinic-acid cake and a mother liquor each time.

This continuous crystallization operation was continued for 7 hours while the temperature of the cold water being supplied to the jacket was being regulated so that the internal temperature of the crystallization tank was kept at 20° C. Thereafter, the continuous feeding of the succinic-acid-containing liquid and the intermittent discharge of the succinic-acid slurry were stopped, and the contents were continuously stirred for further 1 hour while maintaining the temperature of 20° C.

The average power Pv required for stirring per unit volume during the crystallization operation was 1.0 kW/m$^3$, and the amount of the wet succinic-acid cakes obtained in the period from the time when 6 hours had passed since initiation of the continuous crystallization operation to the time when 7 hours had passed since the initiation thereof was 76 g. These wet succinic-acid cakes were suspension-washed with 350 g of cold water, and the resultant slurry was filtered under vacuum. The wet cake thus obtained was vacuum-dried at 80° C. to recover 55 g of the succinic acid.

The dried succinic acid was examined for particle diameter distribution by the method for determination of particle diameter distribution described above. The results thereof are shown in Table 1 below. The amount of ammonium ions was determined. As a result, the amount thereof was found to be 0.2 ppm.

TABLE 1

| Particle diameter distribution of dry succinic acid | | |
|---|---|---|
| Nominal opening size (μm) | Content [wt %] | Minus-sieve content by weight [wt %] |
| >850 | 0.0 | 100.0 |
| 850-710 | 0.1 | 99.9 |
| 710-500 | 24.7 | 75.2 |
| 500-300 | 57.5 | 17.7 |

TABLE 1-continued

Particle diameter distribution of dry succinic acid

| Nominal opening size (μm) | Content [wt %] | Minus-sieve content by weight [wt %] |
|---|---|---|
| 300-150 | 15.8 | 1.9 |
| 150> | 1.9 | 0.0 |
| d20 [μm] | | 306 |
| d50 [μm] | | 400 |
| d80 [μm] | | 535 |
| (d80 − d20)/d50 | | 0.57 |

Example 2-2

Succinic acid was produced in accordance with the same method as in Example 2-1, except that the stirring rotation speed was changed to 400 rpm. The average power Pv required for stirring per unit volume in this case was 0.5 kW/m$^3$. The succinic acid obtained was examined for particle diameter distribution by the method for determination of particle diameter distribution described above, and the results thereof are shown in Table 2 below. The amount of ammonium ions was determined, and was found to be 0.3 ppm.

TABLE 2

Particle diameter distribution of dry succinic acid

| Nominal opening size (μm) | Content [wt %] | Minus-sieve content by weight [wt %] |
|---|---|---|
| >850 | 0.3 | 99.7 |
| 850-710 | 3.7 | 96.0 |
| 710-500 | 49.2 | 46.8 |
| 500-300 | 33.4 | 13.4 |
| 300-150 | 12.4 | 1.0 |
| 150> | 1.0 | 0.0 |
| d20 [μm] | | 332 |
| d50 [μm] | | 512 |
| d80 [μm] | | 634 |
| (d80 − d20)/d50 | | 0.59 |

Example 2-3

Figure 9:
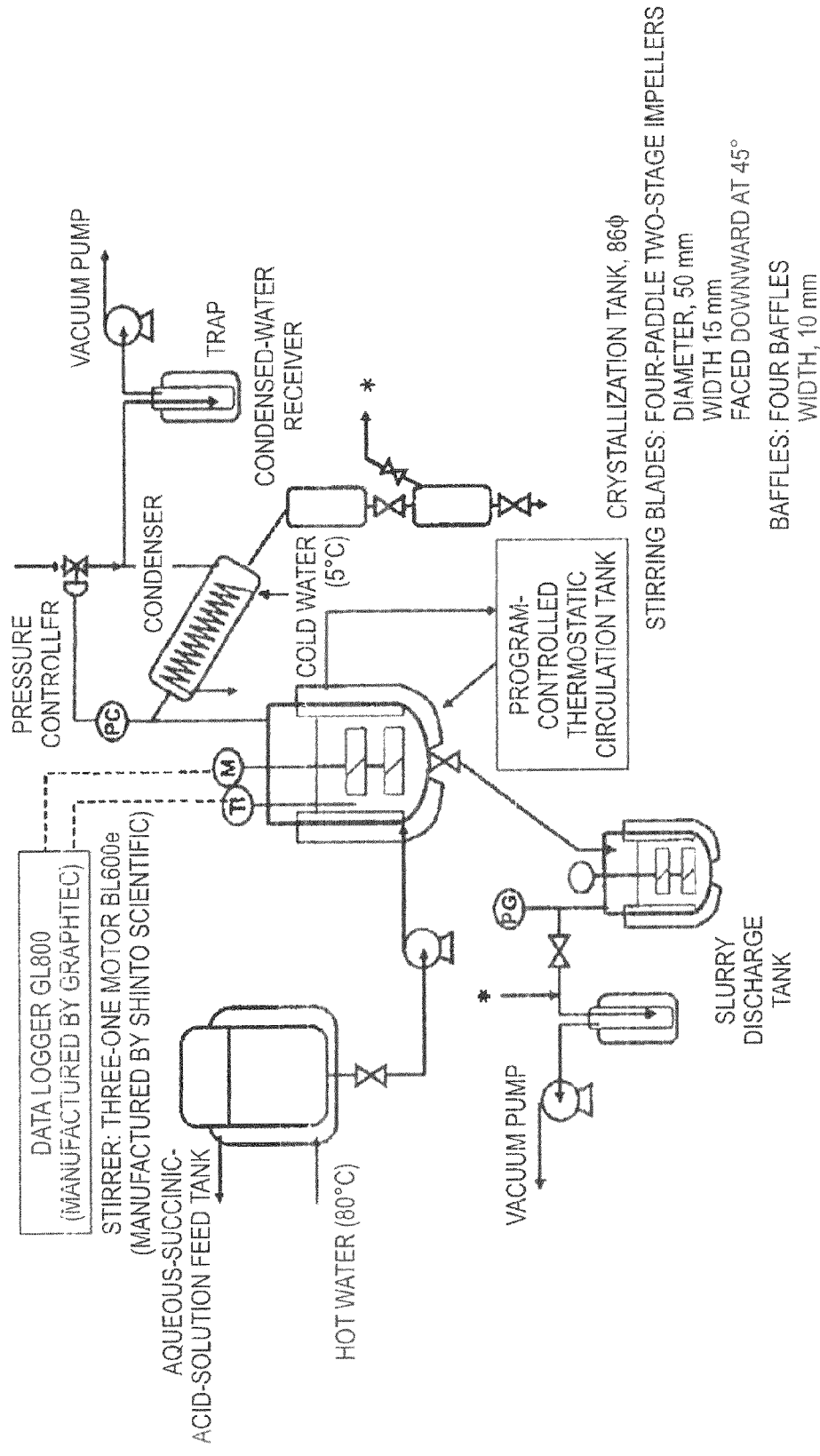
FIG. 9 is a drawing which shows the crystallizer used in Example 2-3.
Figure 10:
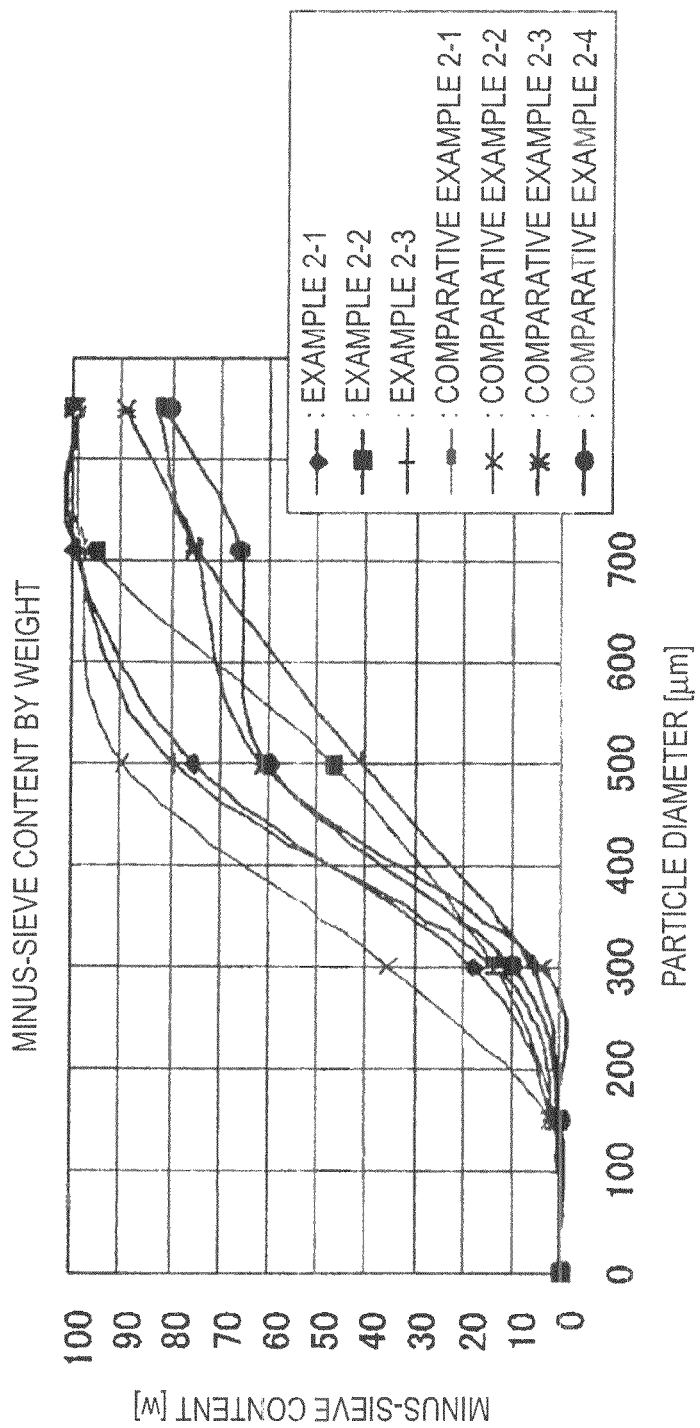
FIG. 10 shows the particle diameter distribution of the particles of succinic acid obtained in each of Examples 2-1 to 2-3 and Comparative Examples 2-1 to 2-4.

The succinic-acid-containing liquid was fed to a crystallizer, such as that shown in FIG. 9, which was constituted of a jacketed separable flask having an inner diameter of 86 mm that was equipped with four baffles having a width of 10 mm and with a stirrer that had four-inclined-paddle impellers which had been arranged in two stages and had a diameter of 50 mm and in which the blades each had a width of 15 mm and faced downward at 45°. The succinic-acid-containing liquid was fed to the crystallizer so that the inside of the crystallizer did not become empty, and vacuum cooling crystallization was conducted in the following manner.

Five hundred milliliters of the succinic-acid-containing liquid was introduced into the stirring tank in which 80° C. hot water was being passed through the jacket. The paddle impellers were rotated at 500 rpm to completely dissolve the succinic acid contained in the succinic-acid-containing liquid to bring the succinic-acid-containing liquid into a state in which no solid matter was observed.

After it was ascertained that the succinic acid had dissolved, the hot-water supply to the jacket was stopped and the internal pressure of the stirring tank was gradually reduced from atmospheric pressure to cool the inside of the tank. The vapor which had vaporized as a result of the pressure reduction was introduced into a condenser, through which 5° C. cold water was being passed, and was thereby condensed and recovered. The pressure was reduced to 2 kPa over about 1 hour to thereby lower the internal temperature of the crystallization tank to 20° C. Thereafter, the contents were continuously stirred for further 1 hour while maintaining the pressure and temperature.

Thereafter, the aqueous succinic acid solution was continuously fed at a rate of 300 mL/min while keeping the internal pressure and temperature of the crystallization tank at 2 kPa and 20° C., respectively. Simultaneously therewith, a succinic-acid slurry was intermittently discharged from the stirring tank to a slurry discharge tank at intervals of about 15 minutes so that the liquid level in the crystallization tank was kept constant.

This continuous crystallization operation was continued for 7 hours while regulating the pressure so that the internal temperature of the crystallization tank was kept at 20° C. Thereafter, the continuous feeding of the succinic-acid-containing liquid and the intermittent discharge of the succinic-acid slurry were stopped, and the pressure was returned to atmospheric pressure. Subsequently, the contents were continuously stirred for 1 hour while keeping the internal temperature of the crystallization tank at 20° C. by passing cold water through the jacket.

The average power Pv required for stirring per unit volume during the crystallization operation was 1.0 kW/m$^3$. The wet succinic-acid cakes obtained in the period from the time when 6 hours had passed since initiation of the continuous crystallization operation to the time when 7 hours had passed since the initiation thereof were suspension-washed with cold water, and the resultant slurry was filtered under vacuum. The wet cake thus obtained was vacuum-dried at 80° C. to recover the succinic acid.

The dried succinic acid was examined for particle diameter distribution by the method for determination of particle diameter distribution described above. The results thereof are shown in Table 3 below. The amount of ammonium ions was determined, and was found to be 0.3 ppm.

TABLE 3

Particle diameter distribution of dry succinic acid

| Nominal opening size (μm) | Content [wt %] | Minus-sieve content by weight [wt %] |
|---|---|---|
| >850 | 0.1 | 99.9 |
| 850-710 | 0.7 | 99.2 |
| 710-500 | 19.8 | 79.4 |
| 500-300 | 65.7 | 13.7 |
| 300-150 | 12.5 | 1.2 |
| 150> | 1.2 | 0.0 |
| d20 [μm] | | 315 |
| d50 [μm] | | 398 |
| d80 [μm] | | 506 |
| (d80 − d20)/d50 | | 0.48 |

Comparative Example 2-1

Succinic acid was produced in accordance with the same method as in Example 2-1, except that the stirring rotation speed was changed to 300 rpm. The average power Pv required for stirring per unit volume in this case was 0.2 kW/m$^3$. The succinic acid obtained was examined for particle diameter distribution by the method for determination of particle diameter distribution described above, and the results thereof are shown in Table 4 below. As shown in Table 4, the succinic acid obtained had a broad particle diameter distribution and the crystals of succinic acid obtained were inferior in uniformity to the succinic acid crystals obtained in the Example. The amount of ammonium ions was determined, and was found to be 0.4 ppm.

TABLE 4

Particle diameter distribution of dry succinic acid

| Nominal opening size (μm) | Content [wt %] | Minus-sieve content by weight [wt %] |
|---|---|---|
| >850 | 17.2 | 82.8 |
| 850-710 | 8.3 | 74.5 |
| 710-500 | 33.6 | 40.9 |
| 500-300 | 34.8 | 6.1 |
| 300-150 | 5.8 | 0.3 |
| 150> | 0.3 | 0.0 |
| d20 [μm] | | 368 |
| d50 [μm] | | 550 |
| d80 [μm] | | 800 |
| (d80 − d20)/d50 | | 0.79 |

Comparative Example 2-2

Succinic acid was crystallized and recovered in accordance with the same method as in Example 2-1, except that Three-One Motor BL1200 (Shinto Scientific Co., Ltd.) was used in place of the Three-One Motor BL600Te, manufactured by Shinto Scientific Co., Ltd., used in Example 2-1 and that the stirring rotation speed was changed to 800 rpm. However, since power required for stirring generally satisfies that (power required for stirring, Pv)∝(stirring rotation speed, n)$^3$, the Pv was regarded as Pv=1×(800/500)$^3$=4 kW/m$^3$.

The contents of the crystallization tank, when in the state of being stirred, were apparently even. However, after the stirring was stopped, it was found that a large amount of bubbles were adherent to the succinic acid crystals and the succinic acid crystals were substantially floating. Even when it was attempted to intermittently discharge the crystals, it was impossible to stably discharge the crystals because the slurry was in an unstable state.

The succinic acid obtained was examined for particle diameter distribution by the method for determination of particle diameter distribution described above, and the results thereof are shown in Table 5 below. As shown in Table 5, the succinic acid obtained had a broad particle diameter distribution and the crystals of succinic acid obtained were inferior in uniformity to the succinic acid crystals obtained in the Example. The content of ammonium ions was 0.3 ppm.

TABLE 5

Particle diameter distribution of dry succinic acid

| Nominal opening size (μm) | Content [wt %] | Minus-sieve content by weight [wt %] |
|---|---|---|
| >850 | 0.9 | 99.1 |
| 850-710 | 0.8 | 98.3 |
| 710-500 | 8.6 | 89.7 |
| 500-300 | 54.4 | 35.3 |
| 300-150 | 32.9 | 2.4 |
| 150> | 2.4 | 0.0 |
| d20 [μm] | | 217 |
| d50 [μm] | | 344 |
| d80 [μm] | | 456 |
| (d80 − d20)/d50 | | 0.69 |

Comparative Example 2-3

Succinic acid was produced in accordance with the same method as in Example 2-1, except that a Maxblend blade having an inner diameter of 63 mm (with no baffle) was used to conduct stirring at 300 rpm. The average power Pv required for stirring per unit volume in this case was 0.3 kW/m$^3$. The succinic acid obtained was examined for particle diameter distribution by the method for determination of particle diameter distribution described above, and the results thereof are shown in Table 6 below. As shown in Table 6, the succinic acid obtained had a broad particle diameter distribution and included coarse particles in a large amount, and the crystals of succinic acid obtained were inferior in uniformity to the succinic acid crystals obtained in the Example.

TABLE 6

Particle diameter distribution of dry succinic acid

| Nominal opening size (μm) | Content [wt %] | Minus-sieve content by weight [wt %] |
|---|---|---|
| >850 | 11.0 | 89.0 |
| 850-710 | 13.4 | 75.6 |
| 710-500 | 14.4 | 61.2 |
| 500-300 | 57.1 | 4.1 |
| 300-150 | 3.6 | 0.5 |
| 150> | 0.5 | 0.0 |
| d20 [μm] | | 345 |
| d50 [μm] | | 456 |
| d80 [μm] | | 753 |
| (d80 − d20)/d50 | | 0.89 |

Comparative Example 2-4

Succinic acid was produced in accordance with the same method as in Example 2-1, except that a draft tube having an inner diameter of 60 mm was inserted into the crystallization tank and that stirring was conducted at 500 rpm with the four-inclined-paddle impellers in which the blades each had a width of 15 mm and faced downward at 45°. The average power Pv required for stirring per unit volume in this case was 0.2 kW/m$^3$. The succinic acid obtained was examined for particle diameter distribution by the method for determination of particle diameter distribution described above, and the results thereof are shown in Table 7 below. As shown in Table 7, the succinic acid obtained had a broad particle diameter distribution and included coarse particles in a large amount, and the crystals of succinic acid obtained were inferior in uniformity to the succinic acid crystals obtained in the Example.

TABLE 7

Particle diameter distribution of dry succinic acid

| Nominal opening size (μm) | Content [wt %] | Minus-sieve content by weight [wt %] |
|---|---|---|
| >850 | 19.2 | 80.8 |
| 850-710 | 14.8 | 66.0 |
| 710-500 | 5.8 | 60.2 |
| 500-300 | 50.3 | 9.9 |
| 300-150 | 9.8 | 0.1 |
| 150> | 0.1 | 0.0 |
| d20 [μm] | | 332 |
| d50 [μm] | | 451 |
| d80 [μm] | | 842 |
| (d80 − d20)/d50 | | 1.13 |

As shown above, the succinic acid produced continuously by the production processes of the invention had excellent uniformity in particle diameter and had a high purity.

Example 3-1

The solution containing succinic acid was subjected to cooling crystallization using a jacketed separable flask, such as that shown in FIG. 8, which had an inner diameter of 86 mm and was equipped with four baffles having a width of 10 mm and with four-inclined-paddle impellers which had been arranged in two stages and had a diameter of 50 mm and in which the blades each had a width of 15 mm and faced downward at 45°. The cooling crystallization was performed so that the inside of the flask did not become empty.

Five hundred milliliters of the solution containing 32% by weight succinic acid was introduced into the stirring tank in which 80° C. hot water was being passed through the jacket. The paddle impellers were rotated at 500 rpm to completely dissolve the succinic acid contained in the succinic-acid-containing solution to bring the solution into a state in which no solid matter was observed.

After it was ascertained that the succinic acid had dissolved, the temperature of the hot water being supplied to the jacket was lowered to 40° C. over about 1 hour to lower the internal temperature of the crystallization tank to 40° C. After the internal temperature became 40° C., the contents were continuously stirred for further 1 hour while maintaining that temperature.

Thereafter, the succinic-acid-containing solution was continuously fed at 250 mL/min while the temperature of the cold water being passed through the jacket was being regulated so that the internal temperature of the crystallization tank was able to be kept at 40° C. Simultaneously therewith, a slurry containing solid succinic acid was intermittently discharged to a slurry discharge tank at intervals of about 15 minutes so that the volume of the succinic-acid slurry in the crystallization tank was substantially constant. The succinic-acid-containing slurry discharged was filtered under vacuum and thereby separated into a wet succinic-acid cake and a mother liquor each time.

This continuous crystallization operation was continued for 7 hours while the temperature of the cold water being supplied to the jacket was being regulated so that the internal temperature of the crystallization tank was kept at 40° C. Thereafter, the continuous feeding of the succinic-acid-containing solution and the intermittent discharge of the succinic-acid slurry were stopped, and the contents were continuously stirred for further 1 hour while maintaining the temperature of 40° C.

The wet succinic-acid cakes obtained in an amount of 124 g in the period from the time when 5 hours had passed since initiation of the continuous crystallization operation to the time when 7 hours had passed since the initiation thereof were suspension-washed with 600 g of cold water. Thereafter, the resultant slurry was filtered under vacuum. The wet cake obtained was vacuum-dried at 80° C. to recover 80 g of succinic acid.

The succinic acid obtained was used as a starting material to produce a polyester in accordance with the [Production of Aliphatic Polyester], and the polymer obtained was evaluated. As a result, the polymer was found to have a YI of 3, a reduced viscosity ($\eta sp/c$) of 2.3, and an amount of terminal carboxyl groups of 24 equivalents per ton.

Example 3-2

Succinic acid was produced in accordance with the same method as in Example 3-1, except that the crystallization temperature was changed to 30° C. Furthermore, the succinic acid obtained was used to produce a polyester, and this polymer was evaluated. As a result, the polymer was found to have a YI of 5, a reduced viscosity ($\eta sp/c$) of 2.2, and an amount of terminal carboxyl groups of 24 equivalents per ton.

Example 3-3

Succinic acid was produced in accordance with the same method as in Example 3-2, except that the rate of feeding the succinic-acid-containing solution to the crystallization tank was changed to 167 mL/min. Furthermore, the succinic acid obtained was used to produce a polyester, and this polymer was evaluated. As a result, the polymer was found to have a YI of 5, a reduced viscosity ($\eta sp/c$) of 2.2, and an amount of terminal carboxyl groups of 24 equivalents per ton.

Comparative Example 3-1

Succinic acid was produced in accordance with the same method as in Example 3-1, except that the crystallization temperature was changed to 20° C. Furthermore, the succinic acid obtained was used to produce a polyester, and this polymer was evaluated. As a result, the polymer was found to have a YI of 10, a reduced viscosity ($\eta sp/c$) of 2.3, and an amount of terminal carboxyl groups of 24 equivalents per ton.

Comparative Example 3-2

Five hundred milliliters (540 g) of the solution containing succinic acid was introduced into the same jacketed separable flask as in Example 3-1, which had an inner diameter of 86 mm and was equipped with four baffles having a width of 10 mm and with four-paddle impellers which had been arranged in two stages and had a diameter of 50 mm and in which the blades each had a width of 15 mm and faced downward at 45°. The contents were kept at 80° C. by passing hot water through the jacket while stirring the contents at 500 rpm. Thereafter, the temperature of the water being passed through the jacket was lowered to 20° C. over 1 hour at a rate of 1° C./min, and the contents were kept being cooled for further 1 hour so that the internal temperature of the crystallization tank was kept at 20° C. Thus, succinic acid was crystallized.

The succinic-acid slurry obtained was filtered and thereby separated into 155 g of a wet succinic-acid cake and 380 g of a mother liquor. The wet succinic-acid cake obtained in an amount of 155 g was introduced into a 1-L beaker together with 700 g of pure water and suspension-washed therein, and the slurry was filtered. The wet cake obtained was vacuum-dried to recover 110 g of succinic acid. The succinic acid obtained was used to produce a polyester, and this polymer was evaluated. As a result, the polymer was found to have a YI of 2, a reduced viscosity ($\eta sp/c$) of 2.3, and an amount of terminal carboxyl groups of 24 equivalents per ton.

Comparative Example 3-3

Succinic acid was produced in accordance with the same method as in Comparative Example 3-2, except that the crystallization temperature was changed to 40° C. Furthermore, the succinic acid obtained was used to produce a polyester, and this polymer was evaluated. As a result, the polymer was found to have a YI of 2, a reduced viscosity ($\eta sp/c$) of 2.4, and an amount of terminal carboxyl groups of 25 equivalents per ton.

As demonstrated above, according to the processes for succinic-acid production which include the step of feeding a succinic-acid-containing solution to a crystallization tank and discharging the solid succinic acid from the crystallization tank while preventing the crystallization tank from becoming empty, a polymer which has been colored little and has a low value of YI can be obtained by regulating the temperature of the succinic-acid-containing liquid present in the crystallization tank to 35-50° C.

Example 4-1

A given amount of succinic acid of a food additive grade (Kawasaki Kasei Chemicals Ltd.) was dissolved in a given amount of 80° C. hot water to prepare a succinic-acid-containing liquid.

Figure 11:
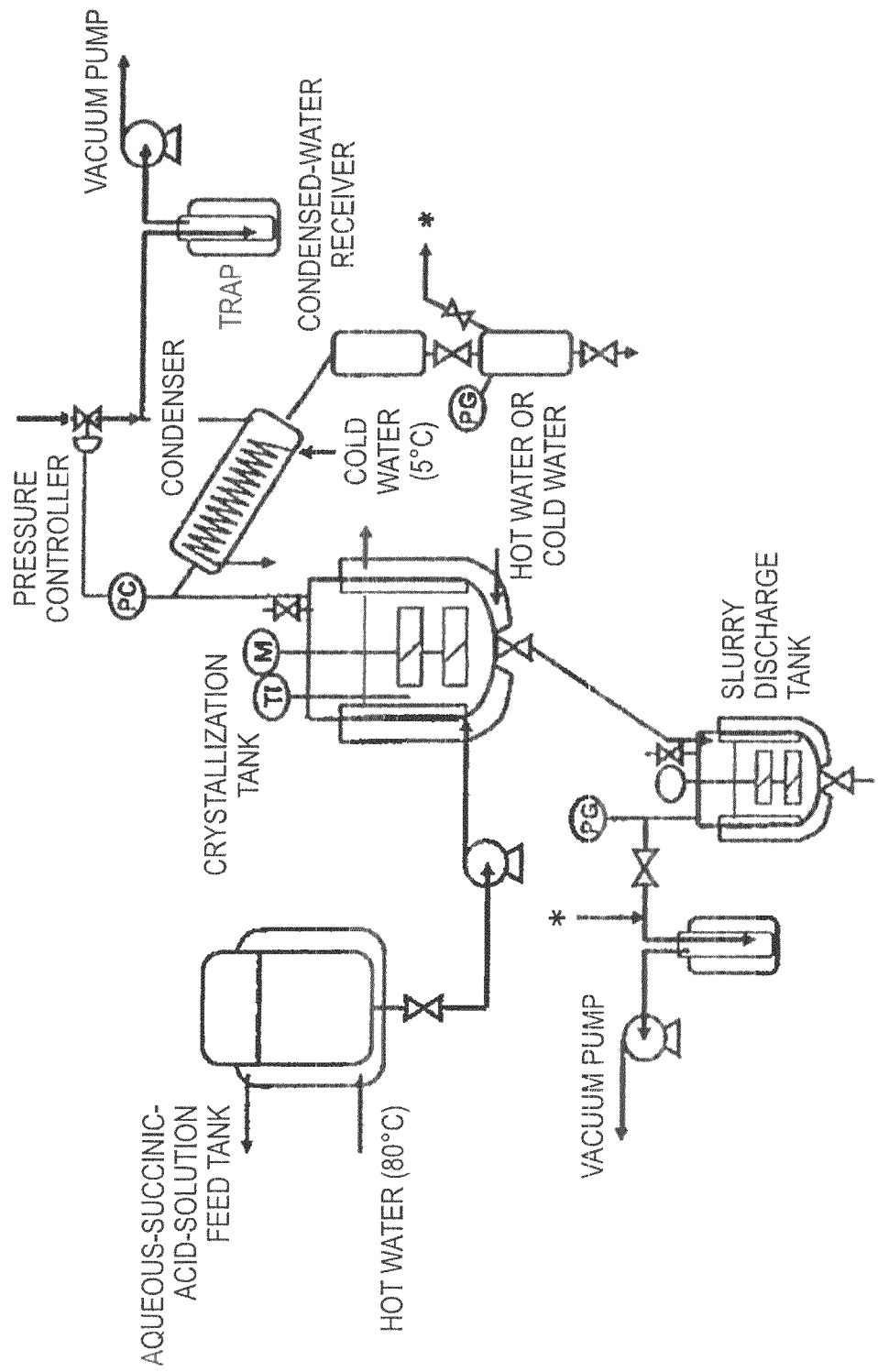
FIG. 11 is a drawing which shows the crystallizer used in Example 4-1 and Comparative Example 4-1.

Crystallization of succinic acid with cooling by adiabatic pressure reduction was conducted in the following manner using a flask having an inner diameter of 86 mm and equipped with a jacket made of glass (thermal conductivity, 1 W/(m·° C.); wall thickness, about 1.5 mm) and a stirring tank that was made of SUS304 stainless steel as provided for in JIS G 4304 (thermal conductivity, 15 W/(m·° C.)) and equipped with four-paddle impellers which had been arranged in two stages and had a diameter of 50 mm and in which the blades each had a width of 15 mm and faced downward at 45° and with four baffles having a width of 10 mm. A flow diagram of the apparatus is shown in FIG. 11.

Five hundred milliliters of a liquid containing 30% by weight succinic acid which had been prepared beforehand was introduced into the stirring tank in which 80° C. hot water was being passed through the jacket. The contents were stirred by rotating the paddle impellers at 500 rpm to completely dissolve the succinic-acid-containing liquid. After it was ascertained that the succinic acid had dissolved, the hot-water supply to the jacket was stopped and the internal pressure of the stirring tank was gradually reduced from atmospheric pressure to cool the inside of the tank. The vapor which had vaporized as a result of the pressure reduction was introduced into a condenser, through which 5° C. cold water was being passed, and was thereby condensed and recovered. The pressure was reduced to 2 kPa over about 1 hour to thereby lower the internal temperature of the crystallization tank to 20° C.

Thereafter, the contents were continuously stirred for further 1 hour while maintaining the pressure and temperature. Subsequently, the succinic-acid-containing liquid was continuously fed at 300 mL/min while keeping the internal pressure and temperature of the crystallization tank at 2 kPa and 20° C., respectively. Simultaneously therewith, a succinic-acid slurry was intermittently discharged from the stirring tank to a slurry discharge tank at intervals of about 15 minutes so that the liquid level in the crystallization tank was kept constant.

This continuous crystallization was continued for 6 hours. Thereafter, the continuous feeding of the succinic-acid-containing liquid and the intermittent discharge of the succinic-acid slurry were stopped, and the contents were continuously stirred for further 1 hour while maintaining the pressure. The slurry was wholly discharged, and the inside of the crystallization tank was examined thereafter. As a result, no conspicuous scale of succinic acid was observed in the inside of the crystallization tank.

Comparative Example 4-1

Using the same apparatus as in Example 4-1, indirect-cooling crystallization of succinic acid was conducted in the following manner. A liquid containing 35% by weight succinic acid which had been prepared beforehand was introduced into the stirring tank in which 80° C. hot water was being passed through the jacket. The contents were stirred by rotating the paddle impellers at 500 rpm to completely dissolve the succinic-acid-containing liquid. After it was ascertained that the succinic acid had dissolved, the temperature of the hot water being supplied to the jacket was lowered to 20° C. over about 1 hour to lower the internal temperature of the crystallization tank to 20° C. After the internal temperature became 20° C., the contents were continuously stirred for further 1 hour while maintaining the temperature.

Thereafter, the succinic-acid-containing liquid was continuously fed at 250 mL/min while the temperature of the cold water being passed through the jacket was being regulated so that the internal temperature of the crystallization tank was able to be kept at 20° C. Simultaneously therewith, a succinic-acid slurry was intermittently discharged from the stirring tank to the slurry discharge tank at intervals of about 15 minutes. At the time when the continuous feeding of the succinic-acid-containing liquid to the crystallization tank was initiated, the temperature of the cold water was 19.0° C.

The continuous crystallization was continued for 6 hours while the temperature of the cold water being supplied to the jacket was being regulated so that the internal temperature of the crystallization tank was kept at 20° C. The temperature of the cold water which was passed through the jacket after the 6 hours was 17.5° C. The continuous feeding of the succinic-acid-containing liquid and the intermittent discharge of the succinic-acid slurry were stopped, and the contents were continuously stirred for further 1 hour while maintaining the temperature of 20° C.

The slurry was wholly discharged, and the inside of the crystallization tank was examined thereafter. As a result, a scale of succinic acid crystals which had a thickness of several millimeters was observed over the whole surface of the inside of the crystallization tank.

Comparative Example 4-2

Figure 12:
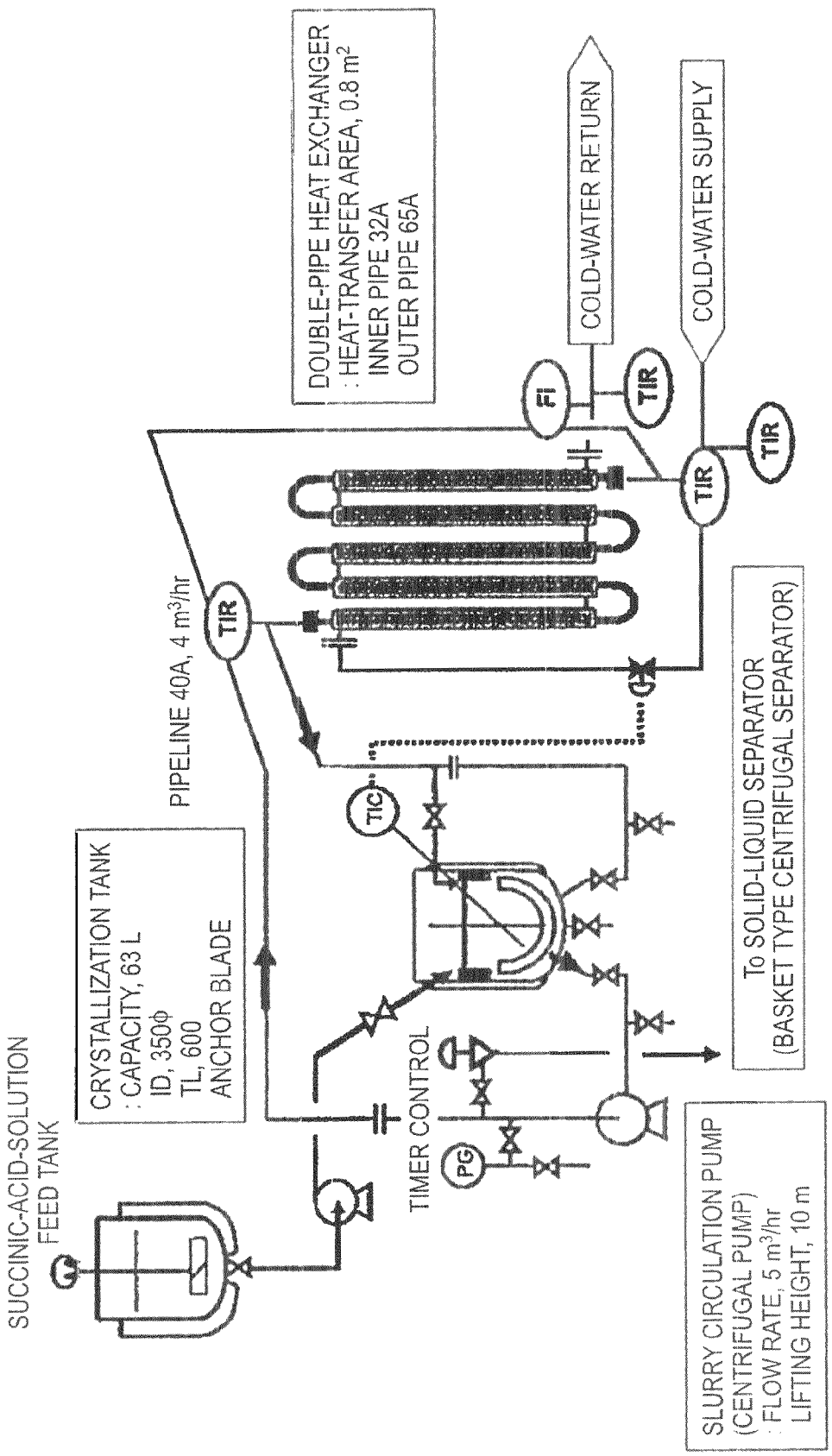
FIG. 12 is a drawing which shows the crystallizer used in Comparative Example 4-2.

Cooling crystallization of succinic acid with an external heat exchanger was conducted in the following manner using a crystallizer equipped with: a complete-mixing stirring tank which was equipped with an anchor blade made of SUS304 and had an inner diameter of 350 mm and a capacity of 63 L (no baffle); an external heat exchanger (double-pipe heat exchange; area of heat-transfer surface, 0.8 m² (the inner pipe had an inner diameter of 35.7 mm, outer diameter of 42.7 mm, and wall thickness of 3.5 mm; the outer pipe had an inner diameter of 67.9 mm, outer diameter of 76.3 mm, and wall thickness of 4.2 mm)); and a centrifugal pump for circulating a slurry through the crystallization tank and the heat exchanger. A flow diagram of the apparatus is shown in FIG. 12.

Succinic acid and water were introduced into the succinic-acid-containing liquid feed tank to prepare a liquid containing 30% by weight succinic acid. Steam was passed through the jacket to regulate the temperature to about 70° C. About 50 L of the succinic-acid-containing liquid prepared was introduced into the crystallization tank, and the contents began to be stirred at 50 rpm. Simultaneously therewith, slurry circulation through the heat exchanger was initiated. While gradually lowering the set temperature of the temperature controller (TIC), the temperature of the crystallization tank was lowered to 20° C. over about 3 hours. Thereafter, the set temperature of the TIC was kept at 20° C. and the contents were aged for about further 1 hour. Subsequently, the succinic-acid-containing liquid was fed from the succinic-acidcontaining liquid feed tank to the crystallization tank at about 25 L/hr and, simultaneously therewith, a slurry was discharged at intervals of about 15 minutes while regulating the liquid level of the crystallization tank. The slurry discharged was subjected to solid-liquid separation with a basket type centrifugal separator to separate the slurry into a wet cake and a mother liquor. This continuous operation was continued for about 4 hours.

The temperature of the coolant inlet was 13° C. immediately after initiation of the continuous operation but declined to 6° C. during the 4-hour continuous operation.

The overall coefficient of heat transfer U of the heat exchanger during the crystallization operation was calculated in accordance with the following calculation formula.

Overall coefficient of heat transfer $U$ [kcal/hr/m$^2$/° C.]=($Q$ [kcal/hr])/(area of heat-transfer surface $S$ [m$^2$])/($\Delta T$[° C.])

In the calculation formula, Q indicates the quantity of heat [kcal/hr] exchanged by the heat exchanger, and is calculated using the following calculation formula.

Quantity of heat exchanged by heat exchanger $Q$ [kcal/hr]=(quantity of heat of coolant $F$ [kg/hr])× (specific heat of coolant [kcal/kg/° C.])×[(coolant outlet temperature [° C.])−(coolant inlet temperature [° C.])]

Furthermore, ΔT indicates the logarithmic mean temperature difference within the heat exchanger, and is calculated using the following calculation formula.

Logarithmic mean temperature difference $\Delta T$ [° C.]= ($\Delta T1-\Delta T2$)/ln($\Delta T1/\Delta T2$)

In the calculation formula,

Heat exchanger inlet temperature difference ΔT1=(heat exchanger process inlet temperature [° C.])−(heat exchanger coolant outlet temperature [° C.])

Heat exchanger outlet temperature difference ΔT2=(heat exchanger process outlet temperature [° C.])−(heat exchanger coolant inlet temperature [° C.]).

The calculated value of overall coefficient of heat transfer U was 350 kcal/hr/m$^2$/° C. immediately after the continuous crystallization, but became 170 kcal/hr/m$^2$/° C. at 4 hours thereafter.

Example 5-1

Succinic acid was produced in the following manner in accordance with the process for succinic-acid production by vaporization crystallization shown in FIG. 13 and FIG. 14.
(1) Raw Liquid Succinic acid (manufactured by Kawasaki Kasei Chemicals Ltd. (food additive grade)) was mixed with tap water in a jacketed raw-material tank 20, and steam was passed through the jacket to thereby keep the inside of the tank 20 at about 70° C. Thus, a 30% by weight aqueous solution of succinic acid was prepared.
(2) Liquid Introduction into Crystallizer 10, etc.

The aqueous succinic-acid solution thus prepared was discharged from the tank 20 with a raw-liquid feed pump P$_1$, diluted to a succinic-acid concentration of about 6.5% by weight by adding tap water thereto, and then fed to a crystallizer 10. The feeding of the aqueous succinic acid solution to the crystallizer 10 was conducted until the liquid level L in the crystallizer 10 came to be above the upper end of the draft tube 2 as shown in FIG. 13(a). Thereafter, the rotating blades 3 and 4 were rotated at 225 rpm. Thus, the aqueous succinic acid solution was circulated along the directions indicated by the arrows in FIG. 13(a).

(3) Reduction of Internal Pressure of Crystallizer 10 and Concentration

The degree of vacuum in the crystallizer 10 was gradually reduced, and the pressure and the liquid temperature were lowered to 2 kPa and 20° C., respectively. The water vapor which had accumulated in the vaporization chamber 8 as a result of vaporization that had accompanied the pressure reduction was discharged through a vapor outlet 1g. Meanwhile, the aqueous succinic acid solution present in the tank 20 was intermittently fed without being diluted with tap water, so that the liquid level L in the crystallizer 10 was kept in a given range. Thus, the aqueous succinic acid solution in the crystallizer 10 was concentrated.
(4) Discharge of Succinic Acid After the concentration of the succinic-acid slurry in the crystallizer 10 had reached 30% by weight, the feeding of the aqueous succinic acid solution from the tank 20 to the crystallizer 10 was changed from intermittent feeding to continuous feeding. The rate of feeding the aqueous succinic acid solution was regulated to 50 L/hr. Furthermore, the slurry in the crystallizer 10 was intermittently discharged through a slurry discharge port 1e while regulating the liquid level L. The slurry discharge was conducted at intervals of 15 minutes (residence time, 2 hours). This succinic-acid discharge operation was continued for 6 hours (3 times the residence time). During this operation, the liquid level L was kept above the upper surface of the draft tube 2 within the crystallizer 10. Incidentally, discharge through a clarified-mother-liquor outlet 1f was not conducted.

The slurry discharged after the discharge operation had been continued over that period was subjected to solid-liquid separation with a basket type centrifugal separator 22 to separate the slurry into a wet cake and a mother liquor. The wet cake recovered was dried in a vacuum dryer (not shown) (80° C., 50 Torr). Subsequently, the particles obtained were examined for particle size distribution in accordance with a sieving method (JIS:Z 8815). A median diameter was obtained from the particle size distribution, and the particle size distribution was approximated by the Rosin-Rammler distribution to calculate a uniformity number. The results thereof are shown in Table 8.

Example 5-2

The same procedure as in Example 5-1 was conducted, except that in (4) above, the rate of feeding the aqueous succinic acid solution was changed to 67 L/hr, the slurry discharge was conducted at intervals of 15 minutes (residence time, 1.5 hours), and this succinic-acid discharge operation was continued for 4.5 hours (3 times the residence time). The results thereof are shown in Table 8.

Example 5-3

The same procedure as in Example 5-1 was conducted, except that the rotation speed of the rotating blades 3 and 4 was changed to 337 rpm. The results thereof are shown in Table 8.

Example 5-4

The same procedure as in Example 5-3 was conducted, except that a slurry of seed crystals of succinic acid was added in (4) in the following manner. The results thereof are shown in Table 8.

(Addition of Seed Crystals of Succinic Acid)

Succinic acid (manufactured by Kawasaki Kasei Chemicals Ltd. (food additive grade)) was pulverized beforehand using a bench cutter mill to obtain succinic-acid seed crystals which had passed through a 100-mesh sieve (150 μm). The seed crystals of succinic acid were added to a saturated aqueous succinic acid solution prepared beforehand, so as to result in a slurry concentration of 30% by weight. Thus, a seed-crystal slurry was prepared.

In (4) above, the seed-crystal slurry was intermittently introduced into the crystallizer 10 at intervals of 30 minutes. The rate of the introduction was 2.5 L/hr (which corresponded to about 5% by weight of the succinic acid discharged from the crystallizer 10).

Example 5-5

The same procedure as in Example 5-4 was conducted, except that the rate of introducing the seed-crystal slurry was changed to 1.2 L/hr (which corresponded to about 2% by weight of the succinic acid discharged from the crystallizer 10). The results thereof are shown in Table 8.

Example 5-6

The same procedure as in Example 5-3 was conducted, except that the aqueous succinic acid solution was externally circulated in (4) in the following manner. The results thereof are shown in Table 8.

(External Circulation of Aqueous Succinic Acid Solution)

In (4) above, a slurry circulation pump $P_2$ (centrifugal pump with an open impeller; discharge pressure, 0.2 MPaG) was operated to conduct external circulation. This circulation was conducted at about 8 m³/hr so that the slurry in the pipeline for slurry circulation (50A) had a linear velocity of 1.0 m/sec. Incidentally, no coolant was passed through the slurry heat exchanger 21.

Example 5-7

Succinic acid was produced in the following manner in accordance with the process for succinic-acid production by cooling crystallization shown in FIG. 15.

As the crystallization tank, use was made of a complete-stirring type (CSTR type) crystallization tank (inner diameter, 350Φ; capacity, 63 L; height, 600 mm) equipped with an anchor blade as a stirring blade and with baffles. As the heat exchanger 33, use was made of a double-pipe heat exchanger (area of heat-transfer surface, 0.8 m²; the inner pipe had an inner diameter of 35.7 mm, outer diameter of 42.7 mm, and wall thickness of 3.5 mm; the outer pipe had an inner diameter of 67.9 mm, outer diameter of 76.3 mm, and wall thickness of 4.2 mm). As the pump 32a, a centrifugal pump was used.

Succinic acid (manufactured by Kawasaki Kasei Chemicals Ltd. (food additive grade)) was mixed with tap water in a jacketed raw-material tank 20, and steam was passed through the jacket to thereby keep the inside of the tank 20 at about 70° C. Thus, a 30% by weight aqueous solution of succinic acid was prepared.

Fifty liters of the aqueous succinic acid solution was fed to the crystallization tank 30 through a raw-liquid feed pipeline 31. The stirrer 30a was rotated at a stirring rotation speed of 50 rpm. The pump 32a was operated to circulate the aqueous succinic acid solution present in the crystallization tank 30 through a circulation pipeline 32 and the heat exchanger 33. This external circulation was conducted at a flow rate of 4 m³/hr (discharge pressure, 0.15 MPa).

Subsequently, a temperature controller (TIC) was used to regulate the flow rate of the coolant of the heat exchanger 33 to thereby lower the temperature of the liquid present in the crystallization tank 30 to 20° C. over 2 hours. Thereafter, the temperature of the liquid in the crystallization tank 30 was kept at 20° C. and the liquid was aged for 1 hour.

Subsequently, while keeping the rate of external circulation at 4 m³/hr, the aqueous succinic acid solution was continuously fed at 50 L/hr through the raw-liquid feed pipeline 31. Simultaneously therewith, the slurry in the crystallization tank 30 was intermittently discharged through a discharge line 34a at intervals of 15 minutes (residence time, 2 hours) while regulating the liquid level. This succinic-acid discharge operation was continued for 6 hours (3 times the residence time).

The slurry discharged after the discharge operation had been continued over that period was subjected to solid-liquid separation with a basket type centrifugal separator to separate the slurry into a wet cake and a mother liquor. The wet cake recovered was dried in a vacuum dryer (80° C., 50 Torr). Subsequently, the particles obtained were examined for particle size distribution in accordance with a sieving method (JIS:Z 8815). A median diameter was obtained from the particle size distribution, and the particle size distribution was approximated by the Rosin-Rammler distribution to calculate a uniformity number. The results thereof are shown in Table 8.

Comparative Example 5-1

Commercial succinic acid (manufactured by Kishida Chemical) was examined for particle size distribution in accordance with a sieving method (JIS:Z 8815). A median diameter was obtained from the particle size distribution, and the particle size distribution was approximated by the Rosin-Rammler distribution to calculate a uniformity number. The results thereof are shown in Table 8.

Comparative Example 5-2

Two hundred grams of 30% by weight aqueous succinic acid solution having a temperature of 70° C. was introduced into a 500-mL jacketed separable flask that was made of glass and had an inner diameter of 86 mm and that was equipped with four baffles having a width of 10 mm and with four-inclined-paddle impellers which had been arranged in two stages and had a diameter of 50 mm and in which the blades each had a width of 15 mm and faced downward at 45°. Hot water having a temperature of 70° C. (program-controlled thermostatic circulation tank) was passed through the jacket, and the contents were kept being stirred at a stirring rotation speed of 300 rpm.

Thereafter, the temperature of the hot water being passed through the jacket was linearly lowered from 70° C. to 20° C. over 2 hours by means of the program-controlled thermostatic circulation tank. After the temperature had declined to 20° C., the contents were aged for further 1 hour. Thereafter, the slurry was filtered with a vacuum filter and separated into a wet cake and a mother liquor. The wet cake was dried in a vacuum dryer, and the resultant particles were examined for particle size distribution in accordance with a sieving method (JIS:Z 8815). A median diameter was obtained from the particle size distribution, and the particle size distribution was approximated by the Rosin-Rammler distribution to calculate a uniformity number. The results thereof are shown in Table 8.

TABLE 8

| | Stirring | | | | Particle size distribution | | | | Addition of seed crystals (wt %) | Pump circulation (m³/hr) |
|---|---|---|---|---|---|---|---|---|---|---|
| | Residence time (hr) | rotation speed (rpm) | Tip speed (m/sec) | Slurry concentration (wt %) | Median diameter (μm) | Uniformity number | Apparatus | Continuous/batch | | |
| Example 5-1 | 2 | 225 | 4.0 | 30 | 547 | 3.63 | DP type | continuous crystallization | — | — |
| Example 5-2 | 1.5 | 225 | 4.0 | 29 | 553 | 3.05 | DP type | continuous crystallization | — | — |
| Example 5-3 | 2 | 337 | 6.0 | 30 | 446 | 3.45 | DP type | continuous crystallization | — | — |
| Example 5-4 | 2 | 337 | 6.0 | 30 | 252 | 3.45 | DP type | continuous crystallization | 5 | — |
| Example 5-5 | 2 | 337 | 6.0 | 29 | 360 | 4.64 | DP type | continuous crystallization | 2 | — |
| Example 5-6 | 2 | 337 | 6.0 | 29 | 224 | 3.38 | DP type | continuous crystallization | — | 8 |
| Example 5-7 | 2 | 50 | 0.8 | 28 | 113 | 3.07 | CSTR type | continuous crystallization | — | 4 |
| Comparative Example 5-1 | — | — | — | — | 368 | 2.19 | — | — | — | — |
| Comparative Example 5-2 | — | 300 | 0.8 | 28 | 584 | 3.28 | CSTR type | Batch crystallization | — | — |

As shown in Table 8, the succinic acid obtained in Examples 5-1 to 5-7 had a uniformity number of 3 or greater and had a narrower distribution and higher uniformity in particle diameter than the succinic acid of Comparative Example 5-1 (uniformity number, 2.19).

The succinic acid obtained in Examples 5-4 to 5-7 had an average particle diameter (median diameter) of 400 μm or less. In contrast, the succinic acid obtained in Comparative Example 5-2 had an average particle diameter (median diameter) of 584 μm, which was too large.

A comparison among Example 5-3 (seed crystals were not added), Example 5-4 (seed crystals were added at 2.5 L/hr), and Example 5-5 (seed crystals were added at 1.2 L/hr) shows that the uniformity number was the greatest in Example 5-4. Furthermore, the larger the amount of the seed crystals added, the smaller the average particle diameter (median diameter).

While the invention has been described in detail and with reference to specific embodiments thereof, it will be apparent to one skilled in the art that various changes and modifications can be made therein without departing from the spirit and scope thereof.

This application is based on a Japanese patent application filed on Mar. 16, 2010 (Application No. 2010-059578), a Japanese patent application filed on Mar. 17, 2010 (Application No. 2010-060674), a Japanese patent application filed on Apr. 1, 2010 (Application No. 2010-085561), a Japanese patent application filed on Apr. 7, 2010 (Application No. 2010-089048), and a Japanese patent application filed on Aug. 11, 2010 (Application No. 2010-179896), the entire contents thereof being incorporated herein by reference.

DESCRIPTION OF REFERENCE NUMERALS

1 Tank
2 Draft tube
3, 4 Rotating blade
5 Baffle plate
6 Rotating shaft
7 Motor
8 Vaporization chamber
10 Crystallizer
20 Jacketed raw-material tank
21 Slurry heat exchanger
22 Condenser
23 Basket type centrifugal separator
25 Clarified-mother-liquor tank
30 Crystallization tank
33 Heat exchanger

The invention claimed is:

1. A process for producing succinic acid, the process comprising:
   feeding a succinic-acid-containing liquid continuously or intermittently to a crystallization tank,
   crystallizing succinic acid from the succinic-acid-containing liquid in the crystallization tank, to obtain crystallized succinic acid, and
   discharging the crystallized succinic acid continuously or intermittently from the crystallization tank,
   wherein:
   the feeding and the discharging are performed so as to keep a liquid level of the crystallization tank within a given range;
   in the crystallizing, seed crystals of succinic acid are introduced continuously or intermittently into the crystallization tank; and
   the seed crystals comprise crystals obtained by pulverizing at least a part of the crystallized succinic acid that has been discharged from the crystallization tank.

2. The process according to claim 1, wherein the crystallization tank comprises a stirrer, and during at least a part of the crystallizing the stirrer is operated such that a stirring power per unit volume of the succinic-acid-containing liquid is 0.4 to 3 kW/m$^3$.

3. The process according to claim 1 or 2, performed such that the succinic-acid-containing liquid in the crystallization tank has a temperature of 25 to 60° C.

4. The process according to claim 3, wherein during the crystallizing, a difference between a temperature of the succinic-acid-containing liquid present in the crystallization tank and a temperature at which the succinic-acid-containing liquid introduced into the crystallization tank becomes a saturated succinic acid solution, is within a range of 10 to 45° C.

5. The process according to claim 1 or 2, wherein the succinic-acid-containing liquid has an average residence time in the crystallization tank of 1 to 5 hours.

6. The process according to claim 1 or 2, further comprising reducing an internal pressure of the crystallization tank, during the crystallizing, to a value lower than a pressure of an ambient atmosphere.

7. The process according to claim 6, wherein the internal pressure of the crystallization tank is 0.5 to 20 kPa.

8. The process according to claim 1, wherein the pulverizing is conducted with a wet pulverizer.

9. The process according to claim 1, wherein the pulverizing is conducted with (i) a circulation unit that discharges a succinic-acid slurry present in the crystallization tank and returns the slurry to the inside of the crystallization tank, or (ii) a pump disposed in a unit that feeds the succinic-acid-containing liquid to the crystallization tank, or both (i) and (ii).

10. The process according to claim 1, wherein the seed crystals have a volume-average particle diameter of 200 μm or less, and an amount of the seed crystals introduced is 0.001 to 20% by weight of an amount of the succinic acid recovered.

11. The process according to claim 1 or 2, wherein the succinic-acid-containing liquid has a succinic-acid concentration of 10 to 45% by weight.

12. The process according to claim 1 or 2, wherein the succinic-acid-containing liquid comprises a solvent having a relative permittivity of 10 or higher.

13. The process according to claim 1 or 2, wherein during the crystallizing, the succinic-acid-containing liquid is cooled by at least 10° C. from a temperature that the succinic-acid-containing liquid had when introduced into the crystallization tank.

14. The process according to claim 1 or 2, wherein the succinic-acid-containing liquid is fed to a liquid phase present in the crystallization tank.

15. The process according to claim 3 or 4, wherein the liquid present in the crystallization tank has a temperature that is lower than a temperature of a wall surface of the crystallization tank.

* * * * *